US008440648B2

(12) United States Patent
Frazer et al.

(10) Patent No.: US 8,440,648 B2
(45) Date of Patent: May 14, 2013

(54) METHODS AND COMPOSITIONS FOR TREATMENT OF INTRAEPITHELIAL NEOPLASIA

(75) Inventors: Neil Frazer, Cary, NC (US); Jonathan Heller, Raleigh, NC (US); Rocio Lopez, Durham, NC (US); Melissa Rhodes, Raleigh, NC (US); Ru Chih C. Huang, Baltimore, MD (US); Richard Dalby, Timonium, MD (US); Niharika Khanna, Ellicott City, MD (US)

(73) Assignees: Erimos Pharmaceuticals LLC, Houston, TX (US); University of Maryland, Baltimore, Baltimore, MD (US); Johns Hopkins University, Baltimore, MD (US)

( * ) Notice: Subject to any disclaimer, the term of this patent is extended or adjusted under 35 U.S.C. 154(b) by 348 days.

(21) Appl. No.: 11/572,349

(22) PCT Filed: Jul. 19, 2005

(86) PCT No.: PCT/US2005/025639
§ 371 (c)(1),
(2), (4) Date: Jan. 19, 2007

(87) PCT Pub. No.: WO2006/014669
PCT Pub. Date: Feb. 9, 2006

(65) Prior Publication Data
US 2008/0004346 A1    Jan. 3, 2008

Related U.S. Application Data

(60) Provisional application No. 60/589,418, filed on Jul. 20, 2004.

(51) Int. Cl.
| A01N 37/12 | (2006.01) |
| A01N 37/44 | (2006.01) |
| A01N 27/00 | (2006.01) |
| A01N 43/00 | (2006.01) |
| A61K 31/195 | (2006.01) |
| A61K 31/015 | (2006.01) |
| A61K 31/33 | (2006.01) |

(52) U.S. Cl.
USPC .................. 514/183; 514/567; 514/764

(58) Field of Classification Search .......... 514/183, 514/567, 764
See application file for complete search history.

(56) References Cited

U.S. PATENT DOCUMENTS

| 2,456,443 A | 12/1948 | Mueller et al. |
| 3,934,034 A | 1/1976 | Manning |
| 4,708,964 A | 11/1987 | Allen |
| 4,745,160 A | 5/1988 | Churchill |
| 4,774,229 A | 9/1988 | Jordan |
| 4,880,637 A | 11/1989 | Jordan |
| 5,008,294 A * | 4/1991 | Neiss et al. ............... 514/731 |
| 5,663,209 A | 9/1997 | Huang |
| 5,827,898 A | 10/1998 | Khandwala |
| 6,039,955 A | 3/2000 | Sinnott |
| 6,214,874 B1 | 4/2001 | Huang |
| 6,291,524 B1 | 9/2001 | Huang |
| 6,365,787 B1 | 4/2002 | Huang |
| 6,417,234 B1 * | 7/2002 | Huang et al. .............. 514/551 |
| 6,545,019 B2 | 4/2003 | Posmantur |
| 6,608,108 B2 | 8/2003 | Huang |
| 6,777,444 B2 | 8/2004 | Huang |
| 6,949,558 B2 | 9/2005 | Altieri et al. |
| 6,958,411 B2 | 10/2005 | Huang |
| 2004/0014721 A1 | 1/2004 | Hensley et al. |
| 2004/0127562 A1 | 7/2004 | Huang |
| 2005/0267208 A1 | 12/2005 | Huang |

FOREIGN PATENT DOCUMENTS

| WO | WO 88/03800 A1 | 6/1988 |
| WO | WO 96/40090 | 12/1996 |

OTHER PUBLICATIONS

Heller et. al., Cancer Research, 2001, 61:5499-5504.*
Kietpeerakool et. al., (Int. J. Clin. Oncol (2009) 14:37-42.*
Thomas C. Wright Jr., MD et al; 2006 Consensus Guidelines for the Management of Women with Cervical Intraepithelial Neoplasia or Adenocarcinoma in situ, AJOG, (2006) p. 340.
Chumnan Kietpeerakook et al; Medical Treatment of Cervical Intraepithelial Neoplasia II,III:an update review, Int J Clin Oncol (2009) 14:37-42.
Kumar, Vinay; et al (2007). Robbins Basic Pathology (8th ed.). Saunders Elsevier. pp. 718-721. ISBN 978-1-4160-2973-1.
Merck Research Laboratories, The Merck Manual of Diagnosis and Therapy, 17th Ed., 1999, pp. 986-995.
Hwu, Jih Ru, et al, Antiviral Activities of Methylated Nordihydroguaiaretic Acids. 1. Synthesis, Structure Identification, and Inhibition of Tat-Regulated HIV Transactivation, J. Med. Chem. 41, pp. 2994-3000, 1998.
Lieberman, S.V., et al, A Synthesis of Nordihydroguaiaretic Acid, Cf, Organic Synthesis, vol. 69, pp. 1540-1541, Wyeth Inst. of Applied Biochemistry, Philadelphia Jan. 17, 1947.
Gnabre, John Noel, "Isolation of anti-HIV-1 lignans from *Larrea tridentate* by counter-current chromatography," Journal of Chromatography A, 719:353-364 (1996).
Schrecker, Anthony W., Meso-Dihydroguaiaretic Acid and its Derivatives. The Laboratory of chemical Pharmacology, National Cancer Institute, pp. 3823-3827, Jul. 20, 1957.
Whitman, Stephanie, et al.., "Structure-Activity Relationship Studies of Nordihydroguaiaretic Acid Inhibitors Toward Soybean, 12-Human, and 15-Human Lipoxygenase." J. Med. Chem. 2002, 45, pp. 2659-2661.
Khanna, Niharika, "Phase I Clinical Trial of Repeat Dose Terameprocol Vaginal Ointment in Healthy Female Volunteers." Sexually transmitted Diseases, Dec. 2008, vol. 35, pp. 1-6.

(Continued)

Primary Examiner — Marcos Sznaidman
(74) Attorney, Agent, or Firm — Roetzel & Andress; Michael J. Keller (57) ABSTRACT

The present invention provides for compositions, kits and methods for treatment of intraepithelial neoplasia, where the compositions include catecholic butanes, which include NDGA derivatives.

13 Claims, 2 Drawing Sheets

OTHER PUBLICATIONS

Khanna, Niharika, "Phase I/II Clinical Safety Studies of Terameprocol Vaginal Ointment." Gynecologic Oncology, 107 (2007), pp. 554-562.

Chang, Chih-Chuan, et al, Reversal of Multidrug Resistance by Two Nordihydroguaiaretic Acid Derivatives, M4N and Maltose-M3N, and Their Use in Combination with Doxorubicin or Paclitaxel. Cancer Chemotherapy Pharmacology (2006) DOI 10.1007/s00280-006-0214-9.

Hansel, Donna E., et al., CDC2/CDK1 Expression in Esophageal Adenocarcinoma and Precursor Lesions Serves as a Diagnostic and Cancer Progression Marker and Potential Novel Drug Target. Am. J. Surg. Pathol., vol. 29, No. 3, Mar. 2005, pp. 390-399.

Heller, Jonathan D., et al., Tetra-O-methyl Nordihydroguaiaretic Acid Induces G2 Arrest in Mammalian Cells and Exhibits Tumoricidal Activity in Vivo. Cancer Research 61, Jul. 15, 2001, pp. 5499-5504.

Lambert, Joshua D., et al., Tetra-O-Methylnordihydroguaiaretic Acid Inhibits Melanoma In Vivo. Cancer Letters, 171 (2001) pp. 47-56.

Lopez, Rocio A., et al., The Anticancer Activity of the Transcription Inhibitor Terameprocol (meso-tetra-O-methyl nordihydroguaiaretic acid) Formulated for Systemic Administration. Anti-Cancer Drugs, 2007, vol. 18 No. 8, pp. 933-939.

Park, Richard, et al., Systemic Treatment with Tetra-O-Methyl Nordihydroguaiaretic Acid Suppresses the Growth of Human Xenograft Tumors. Clin. Cancer Res. 2005; 11 (12), Jun. 15, 2005, pp. 4601-4609.

Mak, Duncan H., et al., Tetra-O-methyl Nordihydroguaiaretic Acid Inhibits Growth and Induces Death of Leukemia Cells Independent of Cdc2 and Survivin. Leukemia & Lymphoma, Jan. 20, 2007, pp, 1-12.

Huang, Ru Chih C., et al., Survivin-Dependent and -Independent Pathways and the Induction of Cancer Cell Death by Tetra-O-methyl Nordihydroguaiaretic Acid. Seminars in Oncology, 2006, 04.010, pp. 479-485.

Chen, Hongshan, et al., Antiviral Activities of Methylated Nordihydroguaiaretic Acids. 2. Targeting Herpes Simplex Virus Replication by the Mutation Insensitive Transcription Inhibitor Tetra-O-methyl-NDGA. J. Med. Chem. 1998, 41, pp. 3001-3007.

Brem, H., "Biodegradable polymer implants to treat brain tumors," Journal of Controlled Release, 74:63-67 (2001).

Craigo, Jodi, Inhibition of Human Papillomavirus Type 16 Gene Expression by Nordihydroguaiaretic Acid Plant Lignan Derivatives. Antiviral Research 47 (2000), pp. 19-28.

Gnabre, John N., et al., Inhibition of Human Immunodeficiency Virus Type 1 Transcription and Replication by DNA Sequence-selective Plant Lignans. Proceedings of Natl. Acad. Sci. USA, vol. 92, Nov. 1995, pp. 11239-11243.

Huang, Ru Chih C., et al., Novel Antiviral Agent Tetraglycylated Nordihydroguaiaretic Acid Hydrochloride as a Host-Dependent Viral Inhibitor. Antiviral Research 58 (2003), pp. 57-64.

Hwu, Jih Ru, et al., Antiviral Activities of Methylated Nordihydroguaiaretic Acids. 1. Synthesis, Structure Identification, and Inhibition of Tat-Regulated HIV Transactivation. J. Med. Chem. 1998, 41, pp. 2994-3000.

Park, Richard, et al., Inhibition of HSV-1 replication and reactivation by the mutation-insensitive transcription inhibitor tetra-O-glycyl-nordihydroguaiaretic acid. Antiviral Research 58 (2003) pp. 35-45.

Fu, Jie, "New polymeric carriers for controlled drug delivery following inhalation or injection," Biomaterials, 23:4425-4433 (2002).

Beletsi, A., et al., "Effect of preparative variables on the properties of poly(dl-lactide-co-glycolide)-methoxypoly(ethyleneglycol) copolymers related to their application in controlled drug delivery," International Journal of Pharmaceutics, 182:187-197 (1999).

Wilhelm, Manfred, "Poly(styrene-ethylene oxide) Block Copolymer Micelle Formulation in Water: A Fluorescence Probe Study," Macromolecules, 24:1033-1040 (1991).

Kim, Eun Hee, "Roscovitine sensitizes glioma cells to TRAIL-mediated apoptosis by downregulation of surviving and XIAP," Oncogene, 23:446-456 (2004).

P.R. Lockman, "Nanoparticle Technology for Drug Delivery Across the Blood-Brain Barrier," Drug Development and Industrial Pharmacy, 28(1):1-12 (2002).

Sankaram Mantripragada, "A lipid based depot (DepoFoam [Registered TM] Technology) for sustained release drug delivery," Progress in Lipid Research, 41:392-406 (2002).

Emmeline Marttin, "Nasal Absorption of Dihydroergotamine from Liquid and Power Formulations in Rabbits," Journal of Pharmaceutical Sciences, 86(7):802-807 (Jul. 1997). (Copyright 1997, American Chemical Society and American Pharmaceutical Associate).

Russell W. McDonald, "Synthesis and anticancer activity of nordihydroguairaretic acid (NDGA) and analogues," Anti-Cancer Drug Design, 16:261-270 (2001).

C.X. Song, "Formulation and characterization of biodegradable nanoparticles for intravascular local drug delivery," Journal of Controlled Release, 43:197-212 (1997).

Milan Stuchlik, "Lipid-based Vehicle for Oral Drug Delivery," Biomed. Papers, 145(2):17-26 (2001).

Xichen Zhang, "Development of amphiphillic diblock copolymers as micellar carriers of taxol," International Journal of Pharmaceutics, 132:195-206 (1996) (Copyright 1996 Elsevier Science B.V.).

Alain Minn, "Drug Transport into the Mammalian Brain: The Nasal Pathway and its Specific Metabolic Barrier," Journal of Drug Targeting., 10(4):285-296 (2002).

L. Mu, "A novel controlled release formulation for the anticancer drug paclitaxel (Taxol [Registered TM]): PLGA nanoparticles containing vitamin E TPGS," Journal of Controlled Release, 86:33-48 (2003).

Kenjiro Ono, "Nordihydroguaiaretic acid potently breaks down preformed Alzheimer's Beta-amyloid fibrils invitro," Journal of Neurochemistry, 81:434-440 (2002).

M.J. Reed, "Effect of masoprocol on carbohydrate and lipid metabolism in a rat model of Type II diabetes," Diabetologia, 42:102-106 (1999).

L. Frolich, "Free Radical Mechanisms in Dementia of Alzheimer Type and the Potential for Antioxidative Treatment," Arzneim.-Forsch./Drug Res. 45(1), Nr. 3a, pp. 443-446 (1995).

Chang, Chih-Chuan, et al., "Tetra-O-methyl nordihydroguaiaretic acid induces growth arrest and cellular apoptosis by inhibiting Cdc2 and survivin expression," PNAS, vol. 101 No. 36, Sep. 7, 2004, pp. 13239-13244.

Lerner, Aaron B., M.D., "Should Vitiligo Be Induced in Paients After Resection of Primary Melanoma?" Arch Dermatol—vol. 113, p. 421, Apr. 1977.

Smart, C.R., "An Interesting Observation on Nordihydroguaiarelic Acid (NSC-4291), NDGA) and a Patient with Malignant Melanoma—A Preliminary Report." Cancer Chemotherapy Reports, Part 1, vol. 53, No. 2, Apr. 1969, pp. 147-151.

Paslin, David, "Melanoma Treatment with Phenolic or Catecholic Compounds," Arch. Dermatol., vol. 113, Sep. 1977, p. 1302.

McCormick, David L., "Nordihydroguaiaretic Acid Suppression of Rat Mammary Carcinogenesis Induced by N-Methyl-N-Nitrosourea." Cancer Letters, 37 (1987) 139-146. Elsevier Scien.

Birkenfeld, Shlomo, "Antitumor Effects of Inibitors of Arachidonic Acid Cascade on Experimentally Induced Intestinal Tumors," Dis. Colon Rectum, 1987, vol. 30,1, pp. 43-46.

Wilson, Diana E., "Effect of nordihydroguaiaretic acid on cultured rat and human glioma cell proliferation." J. Neurosurg 71:551-557, 1989.

Staren, Edgar D., "Lymphokine-Activated Killer Cell Induction in Tumor-Infiltrating Leukocytes From Colon Cancer Patients." Cancer, Dec. 1, 1989, vol. 64, pp. 2238-2242.

Snyder, David S., Antiproliferative Efects of Lipoxygenase Inhibitors on Malignant Human Hematopoietic Cell Lines. Exp. Hematol. 17:6-9 (1989).

Wang, Zhi Y., "Antimutagenic and antitumorigenic activities of nordihydroguaiaretic acid." Mutation Research, 261 (1991) 153-162.

Yu, Akinori, "Anti-promoting Effect of Nordihydroguaiaretic Acid on N-Butyl-N-(4-hydroxybutyl) nitrosamine and Sodium Saccharin-induced Rat Urinary Bladder Carcinogenesis." Jpn. J. Cancer Ses. 83, 944-948, Sep. 1992.

Zamora, John M. "A Comparison of the Cytotoxicity of Nordihydroguaiaretic Acid and its Derivatives." Journal of the Tessennee Academy of Science, 67(4);77-80, Oct. 1992.

Shi, Liming, et al., "Effect of NDGA on Beef Heart Mitochondria and EMT6 Mouse Mammary Carcinoma Cells." Research Communications in Molecular Pathology and Pharmacology, vol. 90, No. 2, pp. 235-254, Nov. 1995.

Avis, Ingalill M., "Growth Control of Lung Cancer by Interruption of 5-Lipoxygenase-mediated Growth Factor Signaling." The Journal of Clinical Investigation, vol. 97, No. 3, Feb. 1996 pp. 806-813.

Ansar, Sabah, "Nordihydroguairetic acid is a potent inhibitor of ferric-nitrilotriacetate-mediated hepatic and renal toxicity, and renal tumour promotion, in mice." Carcinogenesis, vol. 20, No. 4, pp. 599-606, 1999.

Steele, Vernon E., "Lipoxygenase Inhibitors as Potential Cancer Chemopreventives." Cancer Epidemiology, Biomarkers & Prevention, vol. 8, pp. 467-483, May 1999.

Lambert, Joshua D., "Pharmacokinetic analysis by high-performance liquid chromatography of intravenous nordihydrogualaretic acid in the mouse." Journal of Chromatography B, (2001), pp. 85-90.

Walker, Jennifer L., "5-Lipoxyenase and human pulmonary artery endothelial cell proliferation." Am. J. Physiol. Heart Circ. Physiol. 282:H585-H593, 2002.

Tong, Wei-Gang, "Lipoxygenase Inhibitors Attenuate Growth of Human Pancreatic Cancer Xenografts and Induce Apoptosis through the Mitochondrial Pathway." Molecular Cancer Therapeutics, vol. 1, pp. 929-935, Sep. 2002.

Seufferlein, T., "Mechanisms of nordihydroguaiaretic acid-induced growth inhibition and apoptosis in human cancer cells." British Journal of Cancer (2002) 86, pp. 1188-1196.

Hausott, B., "Naturally occurring lignans efficiently induce apoptosis in colorectal tumor cells." J. Cancer Res. Clin. Oncol. (2003) 129:pp. 569-576.

Claudia, Anesini, "In Vivo" and "In Vitro" Antitumoral Action of *Larrea divaricata* Cav. APPTLA 46, pp. 33-40, 1996.

Iida, N., "Suppression of arachidonic acid cascade-mediated apoptosis in aflatoxin B1-induced rat hepatoma cells by glucocorticoids." Carcinogenesis, vol. 19, No. 7, pp. 1191-1202, 1998.

Lambert, Joshua D., "Nordihydroguaiaretic acid: hepatoxicity and detoxification in the mouse." Toxicon 40 (2002), pp. 1701-1708.

Lambert, Joshua D., "Nordihydroguaiaretic Acid: A Review of Its Numerous and Varied Biological Activities." Pharmaceutical Biology 2004, vol. 42 No. 2, pp. 149-158.

Jakovljevic, V.L., "The Effects of Nitric Oxide Synthase—versus Lipoxygenase Inhibition on Coronary Flow and Nitrite Outflow in Isolated Rat Heart." Gn. Physiol. Biophys. (2005), 24, pp. 199-207.

Nie, Daotai, "Mechanisms Regulating Tumor Angiogenesis by 12-Lipoxygenase in Prostate Cancer Cells." Journal of Biological Chemistry, Vo 281, No. 27, pp. 18601-18609, Jul. 7, 2006.

Blecha, J.E., "Inhibition of IGF-1R and lipoxygenase by nordihydroguaiaretic acid (NDGA) analogs." J. Bioorganic & Medicinal Chemistry Letters, 17 (2007) pp. 4026-4029.

Ryan, C.J., "A pilot dose-escalation study of the effects of nordihydroguareacetic acid on hormone and prostate specific antigen levels in patients with relapsed prostate cancer." Journal Compilation, 2008 BJU International, 101, pp. 436-439.

Meyer, Gery E., "Nordihydroguaiaretic Acid Inhibits Insulin-like Growth Factor Signaling, Growth, and Survival in Human Neuroblastoma Cells." Journal of Cellular Biochemistry 102:1529-1541 (2007).

Kim, So Yong, "Regulation of pro-inflammatory responses by lipoxygenases via intracellular reactive oxygen species in vitro and in vivo." Experimental and Molecular Medicine, vol. 40, No. 4, pp. 461-476, Aug. 2008.

Ryan, C.J., "Inhibitory Effects of Nordihydroguaiaretic Acid (NDGA) on the IGF-1 Receptor and Androgen Dependent Growth of LAPC-4 Prostate Cancer Cells." The Prostate 68:1232-1240 (2008).

\* cited by examiner

METHODS AND COMPOSITIONS FOR TREATMENT OF INTRAEPITHELIAL NEOPLASIA

CROSS-REFERENCE TO RELATED APPLICATIONS

This application is a Section 371 of International Application No. PCT/US2005/025639, filed Jul. 19, 2005, which was published in the English language on Feb. 9, 2006, under International Publication No. WO 2006/014669 A2, and also claims the benefit under 35 U.S.C. §119(e)(1) of U.S. provisional application 60/589,418, filed Jul. 20, 2004, which applications are incorporated herein by reference in their entireties.

FIELD OF THE INVENTION

This application relates to methods, compositions and kits containing such compositions for the treatment of intraepithelial neoplasia or dysplasia including, for example, cervical, prostatic, penile, vulvar, anal, oral, or other mucosal neoplasia. In such methods, compositions containing effective amounts of one or more inhibitory compounds, such as those that inhibit Sp1 binding to promoters of genes involved in cell cycle regulation or cell survival, for example, catecholic butanes that include nordihydroguaiaretic acid derivatives, are administered to the subjects.

BACKGROUND OF THE INVENTION

According to the American Association for Cancer Research ("AACR") Task Force on the Treatment and Prevention of Intraepithelial Neoplasia (O'Shaughnessy et al. (2002), "intraepithelial neoplasia ("IEN") is a non-invasive lesion that has genetic abnormalities, loss of cellular control functions, and some phenotypic characteristics of invasive cancer and that predicts for a substantial likelihood of developing invasive cancer." IEN is believed to occur in most epithelial tissue as moderate to severe dysplasia, on the causal pathway leading from normal tissue to cancer.

The AACR Task Force indicates that "[a]lthough several effective endoscopic and surgical treatments for IEN have become standard medical practice, these interventions can confer morbidity and do not treat the entire epithelial field at risk." The Task Force suggests that the "incidence of many epithelial cancers is continuing to rise, the number of individuals at risk is increasing with the aging population . . . " Hence, the Task Force concludes that there is "an urgent need to rapidly develop new treatment and prevention agents for IEN." The Task Force recommends such treatment because of the close association between dysplasia and invasive cancer and because a convincing reduction in IEN burden provides patient benefit by reducing cancer risk and/or by decreasing the need for invasive intervention.

O'Shaughnessy et al. (2002) describes the stages of progression from normal tissue to cancer as including the stages of: initiation of dysplasia, development of mild dysplasia, development of moderate dysplasia, development of severe dysplasia, development of carcinoma in situ ("CIS"), and finally development of cancer (invasive neoplasia).

Thus, for example, for colon cancer, it takes about 5-20 years to progress from normal tissue to the adenoma stage (pre-mild dysplasia), then another 5-15 years to progress from the adenomatous IEN stage, to cancer. For head and neck tumors, it takes about 4-10 years of tobacco use to develop dysplastic oral leukoplakia, and another 6 to 8 years to progress to cancer. For the esophageal tumors, tissues exhibiting the characteristics of Barrett's syndrome progress to severe dysplasia in about 9-13 years, and to cancer in another 3-4 years. For cervical tumors, tissues exhibiting the characteristics of cervical intraepithelial neoplasia ("CIN") are at the initiation of dysplasia stage. The CIN-exhibiting tissues take about 9-13 years to progress to CIN grade 3 or CIS, and another 10-20 years to become cancerous. For lung cancers in general, it takes about 5-20 years for normal tissues to become cancerous. For smokers, lung cancer can be developed over a period of 20-40 cigarette pack-years. For non-melanoma skin cancer, normal tissues progress to the IEN stage in about 30-40 years, and then to cancer in about another 10 years. For breast tumors, tissues exhibiting characteristics of atypical hyperplasia progress to ductal CIS ("DCIS") in about 14-18 years, and from DCIS to cancer in about another 6-10 years. For prostate tumors, it takes about 20 years to progress from normal to prostatic intraepithelial neoplasia ("PIN"), then another 10 years or more to progress to latent cancer stage, and a further 3-15 years to progress to invasive cancer stage. For bladder tumors, it takes about 20 years to progress to transitional cell carcinoma in situ ("TIS"), and less than another 5 years to progress from this IEN stage to invasive cancer.

Colon cancer and rectal cancer (collectively, "colorectal cancer" or "CRC") is known to be the third most common cause of cancer-related death in the United States, after lung and prostate cancer in men, and lung and breast cancer in women. Colorectal carcinogenesis is believed to be a multi-stage process. The first clinically detectable evidence of IEN consists of subtle alterations in the regular pattern of the intestinal crypts known as aberrant crypt foci ("ACF"). "ACF may show loss of wild-type adenomatous polyposis coli ("APC") protein, as well as mutations of K-ras."

Head and neck squamous cell carcinoma ("HNSCC") comprises oral cavity, oral pharynx and laryngeal cancers. The primary risk factors for HNSCC include smoking tobacco and alcohol consumption. The overall survival rate for these cancers (~55%) is not significantly improved over the last three decades. It is believed that although many different changes contribute to epithelial carcinogenesis, histologically, defined IEN lesions are still considered to be a better predictor of cancer risk than any individual genetic lesion. The oral IEN lesions ("OPLs") are white and/or red mucosal patches in the oral cavity or oropharynx that occur in about 1-10% of the adult population in the Western world. "Histological patterns of OPLs vary from hyperkeratosis with hyperplasia to severe dysplasia or CIS."

Barrett's esophagus is believed to be the "primary IEN precursor to esophageal adenocarcinoma." The AACR Task Force in O'Shaughnessy et al. (2002) indicates that esophageal cancer is associated with the third lowest 5-year survival rate among all cancers (behind pancreas and liver). Barrett's esophagus is "a condition in which normal esophageal squamous epithelium is replaced by a metaplastic columnar lining resembling intestinal epithelium," and is believed to be "strongly associated with chronic GERD (gastroesophageal reflux disease)."

Cervical cancer is believed to be the third most common cancer in women worldwide. The precursor lesion to invasive cervical cancer, CIN, is also known as SIL (squamous intraepithelial lesion) of the cervix. "It arises at the junction between the primary columnar epithelium of the endocervix and the squamous epithelium of the ectocervix, a site of continuous metaplastic change." SILs are classified as low grade (LGSIL) and high grade (HGSIL). LGSILs include CIN 1 lesions; HGSILs include CIN 2 and 3 and CIS, according to the Bethesda System. (The Bethesda System for reporting cervical/vaginal cytological diagnoses (1989)) and Kurman, R. J. et al. (1994).

Bronchial intraepithelial neoplasia is the precursor to lung cancer. In the United States, lung cancer is the most common cause of cancer death in both men and women. It is believed that more patients die from lung cancer than from breast, colon, and prostate cancers combined. Like other epithelial malignancies, lung cancers are preceded by a series of precursor lesions. For squamous cell carcinoma ("SCC"), invasive lung cancer develops from first mild, then moderate and severe atypia, then CIS, and then invasive cancer over an average of 10 years. Not much is known about the development of other lung tumor types, but atypical adenomatous hyperplasia of the lung ("AAH") is considered to be the preinvasive lesion of adenocarcinoma.

Non-melanoma skin cancer is the most common type of malignancy. The incidence of skin cancer continues to grow, but mortality attributable to this disease is relatively low. Yet, morbidity can be dramatic because tumors are often disfiguring and located in facial areas, requiring excision of lesions in cosmetically sensitive areas. Keratinocytic non-melanoma skin cancers originate in the epidermis and consist of basal cell carcinoma ("BCC") and squamous cell carcinoma ("SCC"). About 80% of such tumors are BCCs, which appear to originate from basal cells of the epidermis and occasionally those of the infundibular and outer root sheath of the hair follicles. These are slow-growing tumors that are locally invasive but rarely metastasize. SCCs appear to originate in the keratinizing cells of the epidermis. SCCs are generally more aggressive than BCCs and have a much higher potential for metastasis. IEN precursor to
SCC appears as a proliferation of transformed, neoplastic keratinocytes confined to the epidermis and is characterized by thickened, cornified, scaly lesions that develop on the surface of the skin because of improper maturation of keratinocytes.

Breast cancer is believed to be the most common cancer in women excluding BCCs and SCCs of skin and the second most common cause of cancer deaths in women. Breast IEN, which spans the continuum from simple hyperplasia without atypia to CIS, is a recognized risk factor for invasive breast cancer. The predominant phenotype in breast IEN is reportedly a progressive increase in the proportion of cells expressing estrogen receptor ("ER"). An increase in growth factors, growth factor expression, receptor tyrosine kinase activity and proliferation as well as diminished apoptosis is observed in early breast IEN. Women with newly diagnosed advanced TEN, including atypical hyperplasia, lobular CIS ("LCIS"), ductal CIS ("DCIS"), are often offered treatment with 5 years of tamoxifen to reduce the risk of invasive breast cancer.

Prostate cancer is believed to be the most common cancer in males in the United States, accounting for about 29% (180,400) of all new cancers and 11% (31,900) of cancer deaths in males in 2001. Prostate intraepithelial neoplasia ("PIN") is believed to be a morphological and genetic precursor to prostate cancer. PIN lesions are found to be characterized by collections of proliferative prostatic epithelial cells confined within prostatic ducts that exhibit many morphological features of prostate cancer cells. Such features include architectural disorganization, enlarged cell nuclei and nucleoli. PIN lesions are currently classified into two grades, low-grade PIN (formerly PIN 1) and high-grade PIN (HG-PIN, formerly PIN 2 and PIN 3). Current use of the term PIN generally refers only to HGPIN. Evidence that HGPIN is a precursor of prostatic adenocarcinoma includes multifocality of both lesions and the presence of carcinoma in foci of PIN. PIN is usually localized in the peripheral zone of the prostate, where 70% of prostatic carcinomas occur. Both PIN and carcinoma exhibit enhanced proliferative activity (about 3 fold that of benign tissue), cytokeratin immunoreactivity, lectin binding, and loss of blood group antigen. PIN lesions are asymptomatic and cannot be easily diagnosed or detected except through examination of prostate tissue histologically. Available evidence supports the conclusion that presence of PIN on prostate biopsy predicts for an increased risk for prostate cancer and that some PIN give rise to prostate cancers.

Bladder cancer is believed to be the fourth most common cancer in males in the United States, accounting for 6% (39,200) of new cancer cases and 3% (8,300) of cancer-related deaths in 2001. In United States females, the incidence is lower with 2% (15,100) of new cases and less than 2% (4,100) of cancer deaths. Of these cancers that are confirmed histologically, the majority is transitional cell carcinoma ("TCC"). Invasive TCC are thought to arise from one of two IEN precursor lesions, papillary TCC and transitional cell carcinoma in situ ("TIS"). Papillary TCC is the most common bladder tumor, characterized by papillae protruding into the bladder lumen and composed of several layers of urothelial cells. The urothelial cells exhibit a spectrum of cytological atypia and proliferative activity, with grade 1 lesions showing slight cytological atypia and some mitoses, grade 2 showing moderate cytological atypia and some mitoses, and grade 3 lesions showing marked nuclear atypia and frequent mitoses. Lower grade flat lesions in the bladder, often termed mild dysplasia and moderate dysplasia are also recognized. TCC and TIS can be distinguished from invasive carcinoma in that the latter is characterized by progressive penetration of cancer cells through the lamina propria of the bladder urothelium into the underlying musculature. Superficial bladder cancers, i.e., papillary TCC and TIS, and invasive bladder cancers often present with symptoms of hematuria or discomfort.

Vulval intraepithelial neoplasia ("VIN") is defined as the pre-invasive phase of carcinoma of the vulva. It affects 20 to 30 per 100,000 women, with women under 41 constituting 40% of the cases. VIN presents as pruritus vulvae or abnormal skin lesion of the vulva. Management options include local excision and careful monitoring or steroidal treatment. Approximately 6% of the lesions become malignant. It is further believed that if VIN is diagnosed, then there is a greater than 10% risk of neoplasia elsewhere, generally in the cervix.

Pancreatic intraepithelial neoplasia ("PanIN") has been classified into three grades. PanIN 2 and PanIN 3 are believed to be precursors to invasive pancreatic carcinoma. Pancreatic neoplasms can be classified phenotypically based on their cellular lineages, such as ductal, acinar and endocrine phenotypes. Most pancreatic neoplasms are of the ductal type and can be classified as ductal adenocarcinomas. Less common tumors with a ductal phenotype include variants of ductal adenocarcinoma, intraductal papillary mucinous neoplasm including colloid carcinoma, mucinous cystic neoplasm, medullary carcinoma, and other rare tumors. Ductal adenocarcinomas are believed to have developed from ductal proliferative lesions arising in the pancreatic duct system, as described in Kloppel, G. and Luttges, J. (2004) and Takaori, K. et al. (2004).

Other intraepithelial neoplasias that are precursors to invasive cancers have been reported. For example, anal intraepithelial neoplasia ("AIN") presenting as bowenoid papulosis and perianal Bowen disease is believed to be a precursor lesion for invasive squamous cell carcinoma, as described in Wacker, J. and Hartschuh, W. (2004). Testicular intraepithelial neoplasia ("TIN") is believed to be a precursor of testicular germ cell tumors, as described in Dieckmann, K. P. and Pichlmeier, U. (2004). Penile intraepithelial neoplasia ("PenileIN") may be a precursor to high-grade PenileIN and anogenital carcinoma, as described in Aynaud, O. and Bergeron, C. (2004). Conjunctival-corneal intraepithelial neoplasia ("CCIN") is described in Dudney, B. W. and Malecha, M. A. (2004).

Jordan et al. in U.S. Pat. No. 5,008,294 claims the use of certain catecholic butanes for "inhibiting the growth of a tumor which comprises topically administering to the situs of the tumor of a mammal in need of said treatment an effective amount of a composition comprising at least 1 catecholic butanes" of a specified formula. Jordan et al. further claims treatment for tumors of the skin, keratosis of the skin, and actinic keratosis.

McDonald, R. W. wt al. (2001) synthesized five analogues of NDGA with different lengths of carbon bridge between the two catechol moieties and five analogues of NDGA containing only one hydroxyl group on each aromatic ring.

Huang et al., in U.S. Pat. No. 6,365,787 and U.S. Pat. No. 5,663,209, claim certain novel NDGA derivatives that were isolated from Larrea tridentate and use thereof for the suppression of Tat transactivation of a lentivirus in a cell. Hwu, J. R. et al. (1998) described the synthesis of mono-, di-, tri-, and tetra-O-methylated NDGA and isolation of such in pure forms.

Huang et al., in U.S. Pat. No. 6,214,874, further claim, among other things, methods for treating HPV-induced tumor comprising application of at least one NDGA derivative of a specified formula. Additionally, in U.S. Pat. No. 6,417,234, Huang et al. describes, among other things, a method of treating tumors using at least one NDGA derivative of a specified formula. In U.S. Pat. No. 6,608,108, Huang et al. claim, among other things, methods of inhibiting survivin production in a eukaryotic cell cycle and methods of stimulating apoptosis in a cell expressing CDC-2 and survivin.

There is an urgent medical need to develop compositions, kits and methods for treatment of intraepithelial neoplasia of all epithelial cell types so as to reduce the morbidity and mortality of cancer.

SUMMARY OF THE INVENTION

It is one of the objects of the present invention to provide methods, kits and compositions for treatment of intraepithelial neoplasia.

It is another one of the objects of the present invention to provide formulations for the delivery of the compositions as above.

It is a further one of the objects to provide for methods of delivery of the compositions as above for such treatment.

In accordance to such objects, there is provided the present invention as follows. In one embodiment, the invention is directed to a pharmaceutical composition for treatment of intraepithelial neoplasia or dysplasia. The composition comprises at least one compound that inhibits binding of a transcription factor to a regulatory region of a gene involved in regulation of cell cycle or a gene involved in cell survival and a pharmaceutically acceptable carrier or excipient such as, for example, DMSO, saline, ethanol, phosphate buffered saline, Cremaphor, ethanol, water or mixtures thereof, wherein the composition is formulated for delivery to situs of the intraepithelial neoplasia or dysplasia. In certain embodiments, the transcription factor is Sp1 or E2F1.

In certain embodiments, the intraepithelial neoplasia or dysplasia is other than actinic keratosis or keratosis of the skin. In other embodiments, the intraepithelial neoplasia or dysplasia is other than an intraepithelial neoplasia of the skin.

In yet other embodiments, the intraepithelial neoplasia or dysplasia is mucosal.

In still other embodiments, the intraepithelial neoplasia or dysplasia is cervical.

In other embodiments, the intraepithelial neoplasia or dysplasia is prostatic.

In additional embodiments, the intraepithelial neoplasia or dysplasia is penile. In further embodiments, the intraepithelial neoplasia or dysplasia is testicular.

In further embodiments, the intraepithelial neoplasia or dysplasia is vulvar.

In yet additional embodiments, the intraepithelial neoplasia or dysplasia is oral.

In further embodiments, the intraepithelial neoplasia or dysplasia is anal.

In additional embodiments, the intraepithelial neoplasia or dysplasia is pancreatic.

In further embodiments, the intraepithelial neoplasia or dysplasia is lung or pulmonary.

In other embodiments, the intraepithelial neoplasia or dysplasia is breast.

In still further embodiments, the intraepithelial neoplasia or dysplasia is colon.

In additional embodiments, the intraepithelial neoplasia or dysplasia is colorectal.

In additional embodiments, the intraepithelial neoplasia or dysplasia is head and neck.

In further embodiments, the intraepithelial neoplasia or dysplasia is esophageal.

In still further embodiments, the intraepithelial neoplasia or dysplasia is skin.

In additional embodiments, the intraepithelial neoplasia or dysplasia is conjunctival-corneal.

In further embodiments, the intraepithelial neoplasia or dysplasia is bladder.

In additional embodiments of the above, the compound in the composition is a catecholic butane having a structural formula of Formula I:

wherein $R_1$ and $R_2$ are independently —H, a lower alkyl, a lower acyl, an alkylene or an amino acid residue or substituted amino acid residue or salt thereof; $R_3$, $R_4$, $R_5$, $R_6$, $R_{10}$, $R_{11}$, $R_{12}$ and $R_{13}$ are independently —H or a lower alkyl; and $R_7$, $R_8$ and $R_9$ are independently —H, —OH, a lower alkoxy, a lower acyloxy, or any two adjacent groups together may be an alkyene dioxy, and optionally, —$OR_1$, —$OR_2$, $R_7$, $R_8$ and $R_9$ are each an amino acid residue or a substituted amino acid residue or salt thereof.

In certain embodiments, the compound is other than NDGA.

In additional embodiments, the compound has a structural formula of Formula II:

wherein $R_1$, $R_2$, $R_3$ and $R_4$ independently represent —OH, a lower alkoxy, for example, —OCH$_3$, a lower acyloxy, for example, —O(C=O)CH$_3$, or an amino acid residue, or a substituted amino acid residue or a salt thereof such as, a dimethyl-substituted amino acid residue, for example, —O(C=O)CH$_2$N(CH$_3$)$_2$ or —O(C=O)CH$_2$N$^+$(CH$_3$)$_2$.Cl$^-$; and $R_5$, $R_6$ independently represent —H or an alkyl such as a lower alkyl, for example, —CH$_3$. In one embodiment, $R_5$ and $R_6$ are each independently —CH$_3$. In another embodiment, $R_5$ and $R_6$ are each independently —H.

In certain embodiments of the above, $R_1$, $R_2$, $R_3$ and $R_4$ are not each —OH simultaneously.

In yet further embodiments, the compound is tetra-O-methyl NDGA ($M_4N$), tri-O-methyl NDGA ($M_3N$), or di-O-methyl NDGA ($M_2N$).

In additional embodiments, each of $R_1$, $R_2$, $R_3$ and $R_4$ independently represent an N,N-dimethyl substituted amino acid residue or a salt thereof.

In further embodiments, each of $R_1$, $R_2$, $R_3$ and $R_4$ independently represent —O(C=O)CH$_2$N(CH$_3$)$_2$ or —O(C=O)CH$_2$N$^+$(CH$_3$)$_2$.Cl$^-$.

In certain embodiments, the composition comprises a rinse such as an oral rinse, a wash such as a bladder wash, a cream, a lotion, a gel including an adhesive gel, a patch, such as an mucosal patch, a spray such as an oral spray, an ointment, a solid such as a tablet, an aerosol, an inhalant such as a powder or spray, a foam, an enema, a suppository, or a liquid including an injectable liquid or in drops such as topical ocular drops.

In additional embodiments, the gene is a gene of CDC (cell division cycle) family such as CDC2 or CDC6, a gene of histone family, a gene of Bub family such as Bub1, a gene of cyclin family such as cyclin A2, a gene of cyclin family such as cyclin C, cyclin E1, cyclin F, a gene of E2F family such as E2F1, a gene of topoisomerase family such as TOP2A, a gene of VEGF family, or a gene of BRCA family. In certain embodiments, the cyclin family comprises cyclin-dependent kinase such as cyclin dependent kinase 7, or CDKN3.

In further embodiments, the gene is a proliferating cell nuclear antigen (PCNA), a cysteine protease, a human cytokine receptor such as IL-2 receptor, dihydrofolate reductase (DHFR), polo-like kinase, thymidine phosphorylase (TP), replication factor such as RFC4, or ribonucleotides reductase such as RRM2.

In yet further embodiments, the intraepithelial neoplasia or dysplasia is associated with a viral infection. In certain embodiments, the virus is HPV, HSV, EBV, HBV, JC virus, Varicella-zoster virus, adenovirus, parvovirus, or a lenti-virus.

In additional embodiments, the gene involved in survival is survivin.

In certain embodiments, the composition is formulated for administration intravenously, or orally, or buccally, or by inhalation, or intranasally, or intraperitoneally, or subcutaneously, or intravaginally, or by implantation such as in a pessary.

In yet additional embodiments, the composition is formulated for administration or onto the surface of the neoplasia or dysplasia, provided that the lesion is other than actinic keratosis.

In further embodiments, the composition is formulated for administration onto the surface of the neoplasia or dysplasia, provided that the lesion is other than premalignant tumors of the skin.

In additional embodiments, the compound is for application onto the surface of the neoplasia or dysplasia via delivery by inhalation, by intranasal administration, or as a rinse or a wash, or as a suppository or an enema and the compound is present in the composition at a concentration in a range of about 0.05 wt % to about or less than about 30 wt %, optionally, the concentration of the compound is about or less than about 27.5 wt %, or 25 wt %, or 22.5 wt %, or 20 wt %, or 17.5 wt %, or 15 wt %, or 12.5 wt %, or 10 wt %, or 7.5 wt %, or 5 wt %, or 2.5 wt %, or 1.25 wt %.

In further embodiments, the compound is for administration intravenously, intraperitoneally, or subcutaneously and is present in the composition at a concentration in a range of about 0.1 mg/ml to about or less than about 500 mg/ml, optionally, the concentration is in a range of about 0.5 mg/ml to about or less than 475 mg/ml, or about 1 mg/ml to about or less than 400 mg/ml, or about 2 mg/ml to about or less than 375 mg/ml, or about 5 mg/ml to about or less than 350 mg/ml, or about 7.5 mg/ml to about or less than 325 mg/ml, or about 10 mg/ml to about or less than 300 mg/ml, or about 12.5 mg/ml to about or less than 275 mg/ml, or about 15 mg/ml to about or less than 250 mg/ml, or about 17.5 mg/ml to about or less than 225 mg/ml, or about 20 mg/ml to about or less than 200 mg/ml, or about 25 mg/ml to about or less than 175 mg/ml, or about 50 mg/ml to about or less than 150 mg/ml, or about 75 mg/ml to about or less than 125 mg/ml, or about 90 mg/ml to about or less than 120 mg/ml.

In additional embodiments, the compound is for administration orally, for example, as a tablet, and the compound is present in the composition at a concentration of not less than about 98 wt %, or about 95 wt %, or about 90 wt %, or 80 wt %, or 70 wt %, or 60 wt %, or 50 wt %, or 40 wt %, or 30 wt %, or 20 wt %, or 10 wt %, or 5 wt %, or about 2 wt % A, or about 1 wt %.

In further embodiments, the invention is directed to a method of treatment of intraepithelial neoplasia in a subject comprising the steps of:
(a) providing any one of the composition above; and
(b) administering the composition to the subject.

In certain embodiments, the subject is in need of treatment.

In additional embodiments, the composition is administered orally, buccally, topically, intravenously, subcutaneously, intraperitoneally, intranasally, or by inhalation.

In yet further embodiments, the composition is administered as a solid such as a tablet or a powder, a patch such as a mucosal patch, a rinse such as an oral rinse, a wash such as a bladder wash, a spray such as an oral spray, a cream, a lotion, an ointment, a gel including an adhesive gel, an inhalant such as a powder or a spray, a foam, an enema, a suppository, or a liquid such as an ingestible or injectable liquid, or drops such as ocular drops.

In additional embodiments, the step of administering the composition to the subject comprises administering the compound to the subject at a dose in the range of about 0.5 mg/kg to about or less than about 300 mg/kg, or about 1 mg/kg to about or less than about 275 mg/kg, or about 5 mg/kg to about or less than 250 mg/kg, or about 7.5 mg/kg to about or less than 225 mg/kg, or about 10 mg/kg to about or less than 200 mg/kg, or about 25 mg/kg to about or less than 175 mg/kg, or about 50 mg/kg to about or less than 150 mg/kg, or about 75 mg/kg to about or less than 125 mg/kg, or about 90 mg/kg to about or less than 100 mg/kg.

In certain embodiments, the step of administering the composition to the subject comprises administering the compound to the subject at a dose in the range of about 0.5 mg/cm$^2$ on the basis of the size of the neoplasia, to about or less than about 300 mg/cm$^2$, or about 1 mg/cm$^2$ to about or less than about 275 mg/cm$^2$, or about 5 mg/cm$^2$ to about or less than 250 mg/cm$^2$, or about 7.5 mg/cm$^2$ to about or less than 225 mg/cm$^2$, or about 10 mg/cm$^2$ to about or less than 200 mg/cm$^2$, or about 25 mg/cm$^2$ to about or less than 175 mg/cm$^2$, or about 50 mg/cm$^2$ to about or less than 150 mg/cm$^2$, or about 75 mg/cm$^2$ to about or less than 125 mg/cm$^2$, or about 90 mg/cm$^2$ to about or less than 100 mg/cm$^2$.

In further embodiments, the composition is formulated as a nanoparticle composition, a liposomal composition, a micellar composition, an emulsion, In yet further embodiments, the invention is directed to a kit for treatment of intraepithelial neoplasia comprising any one of the compositions described above, instructions for use of the composition and, optionally, an applicator for administration of the composition.

DETAILED DESCRIPTION OF THE INVENTION

The present invention provides for compositions, kits and methods for treatment of intraepithelial neoplasia or dysplasia. The invention can be more clearly understood in light of the following definitions:

The term "about" as used herein in reference to a concentration or dose means the specified number up to ±10%-20%.

The term "active pharmaceutical ingredient" or "API" as used herein means the catecholic butane or NDGA derivative present in the pharmaceutical compositions being claimed herein.

"Alkylene dioxy" as used herein refers to methylene or substituted methylene dioxy or ethylene or substituted ethylene dioxy.

"Amino acid residue or substituted amino acid residue or salt thereof" in reference to one of the —R groups in Formula I or Formula II is an amino acid residue or a substituted amino acid residue or salt of an amino acid residue or salt of a substituted amino acid residue including but not limited to: alanine, arginine, asparagine, aspartate, cysteine, glutamate, glutamine, glycine, histidine, isoleucine, leucine, lysine, methionine, phenylalanine, proline, serine, threonine, tryptophan, tyrosine, valine, 5-hydroxylysine, 4-hydroxyproline, thyroxine, 3-methylhistidine, ∈-N-methyllysine, ∈-N,N,N-trimethyllysine, aminoadipic acid, γ-caroxyglutamic acid, phosphoserine, phosphothreonine, phosphotyrosine, N-methylarginine, N-acetyllysine, and an N,N-dimethyl-substituted amino acid residue or a salt thereof, such as a chloride salt.

The "buffer" suitable for use herein includes any buffer conventional in the art, such as, for example, Tris, phosphate, imidazole, and bicarbonate.

"Catecholic butane" as used herein means a compound of Formula I:

wherein R$_1$ and R$_2$ are independently —H, a lower alkyl, a lower acyl, an alkylene or an amino acid residue or substituted amino acid residue or salt thereof; R$_3$, R$_4$, R$_5$, R$_6$, R$_{10}$, R$_{11}$, R$_{12}$ and R$_{13}$ are independently —H or a lower alkyl; and R$_7$, R$_8$ and R$_9$ are independently —H, —OH, a lower alkoxy, a lower acyloxy, or any two adjacent groups together may be an alkyene dioxy. In one embodiment, —OR$_1$, —OR$_2$, R$_7$, R$_8$ and R$_9$ are each an amino acid residue or a substituted amino acid residue or salt thereof.

A "gene" as used herein means an open reading frame encoding a protein or polypeptide, for example, an mRNA, a cDNA, or genomic DNA that may or may not include intervening introns or adjacent 5' or 3' untranslated regions involved in the regulation of expression.

The term "a gene involved in regulation of cell cycle" means a gene that encodes a protein the presence of which is necessary for a cell to progress through its cell cycle. An example of such a gene is CDC2.

The term "a gene involved in cell survival" means a gene that encodes a protein the presence of which is necessary for the cell to maintain its viability. An example of such a gene that encodes a survival factor, e.g., survivin, or a gene involved in DNA repair, or human telomerase reverse transcriptase.

"Lower acyl" means C$_1$-C$_6$ acyl, optionally, C$_1$-C$_3$ acyl.
"Lower alkyl" means C$_1$-C$_6$ alkyl, optionally, C$_1$-C$_3$ alkyl.
"NDGA" means nordihydroguaiaretic acid.
"NDGA derivative" as used herein means a derivative of NDGA in which one or more of the —OH groups are substituted, as in Formula II:

wherein R$_1$, R$_2$, R$_3$ and R$_4$ are independently —OH, a lower alkoxy, a lower acyloxy, or an amino acid residue or substituted amino acid residue or salt thereof but are not each —OH simultaneously; and R$_5$, R$_6$ are independently —H or an alkyl such as a lower alkyl. The term includes, for example, a compound in which R$_1$, R$_2$, R$_3$ and R$_4$ are each —OCH$_3$, or —O(C=O)CH$_3$ or —O(C=O)CH$_2$N(CH$_3$)$_2$ or —O(C=O)CH$_2$N$^+$(CH$_3$)$_2$.Cl$^-$; and R$_5$, R$_6$ are each —H or each a lower alkyl. In one embodiment of the invention, R$_5$, R$_6$ are each —CH$_3$ or —CH$_2$CH$_3$.

A "regulatory region of a gene" as used herein means a region upstream of the translational start of a gene that includes a binding site for one or more transcription factors, a promoter, an enhancer, and the like.

A "substantially purified" compound in reference to the catecholic butanes or NDGA derivatives for administration herein is one that is substantially free of compounds that are not the catecholic butane or NDGA derivatives of the present invention (hereafter, "non-NDGA materials"). By substantially free is meant at least 50%, preferably at least 70%, more preferably at least 80%, even more preferably at least 90% free and still more preferably at least 95% free of non-NDGA materials.

As used herein, the terms "treatment," "treating," and the like, refer to obtaining a desired pharmacologic and/or physiologic effect. The effect may be prophylactic in terms of completely or partially preventing a condition or disease or symptom thereof and/or may be therapeutic in terms of a partial or complete cure for a condition or disease and/or adverse affect attributable to the condition or disease. "Treatment," thus, for example, covers any treatment of a condition or disease in a mammal, particularly in a human, and includes: (a) preventing the condition or disease from occurring in a subject which may be predisposed to the condition or disease but has not yet been diagnosed as having it; (b) inhibiting the condition or disease, such as, arresting its development; and (c) relieving, alleviating or ameliorating the condition or disease, such as, for example, causing regression of the condition or disease.

A "pharmaceutically acceptable carrier" refers to a non-toxic solid, semisolid or liquid filler, diluent, encapsulating material or formulation auxiliary of any conventional type. A "pharmaceutically acceptable carrier" is non-toxic to recipients at the dosages and concentrations employed, and is compatible with other ingredients of the formulation. For example, the carrier for a formulation containing the present catecholic butane or NDGA derivatives preferably does not include oxidizing agents and other compounds that are known to be deleterious to such. Suitable carriers include, but are not limited to, water, dextrose, glycerol, saline, ethanol, buffer, dimethyl sulfoxide, Cremaphor EL, phosphate buffered saline and combinations thereof. The carrier may contain additional agents such as wetting or emulsifying agents, or pH buffering agents. Other materials such as anti-oxidants, humectants, viscosity stabilizers, and similar agents may be added as necessary.

Pharmaceutically acceptable salts herein include the acid addition salts (formed with the free amino groups of the polypeptide) and which are formed with inorganic acids such as, for example, hydrochloric or phosphoric acids, or such organic acids as acetic, mandelic, oxalic, and tartaric. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, and histidine.

The term "pharmaceutically acceptable excipient," includes vehicles, adjuvants, or diluents or other auxiliary substances, such as those conventional in the art, which are readily available to the public. For example, pharmaceutically acceptable auxiliary substances include pH adjusting and buffering agents, tonicity adjusting agents, stabilizers, wetting agents and the like.

The terms "subject," "host," and "patient," are used interchangeably herein to refer to an animal being treated with the present compositions, including, but not limited to, simians, humans, felines, canines, equines, bovines, porcines, ovines, caprines, mammalian farm animals, mammalian sport animals, and mammalian pets.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

All publications mentioned herein, including patents, patent applications, and journal articles are incorporated herein by reference in their entireties including the references cited therein, which are also incorporated herein by reference in their entireties.

It must be noted that as used herein, the singular forms "a", "an", and "the" include plural referents unless the context clearly dictates otherwise. Thus, for example, reference to "a compound" includes a plurality of such compounds and reference to "the NDGA Compound" includes reference to one or more NDGA Compounds and equivalents thereof known to those skilled in the art.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The invention described below is given by way of example only and is not to be interpreted in any way as limiting the invention.

Preparation of Catecholic Butanes

The catecholic butanes of the present invention can be prepared by any method know in the art. For example, such compounds can be made as described in U.S. Pat. No. 5,008,294.

Preparation of the NDGA Derivatives

The NDGA derivatives and formulations thereof can be made by any process conventional in the art. For example, the NDGA derivatives can be made as described in, U.S. Pat. No. 5,008,294 (Jordan et al., issued Apr. 16, 1991); U.S. Pat. No. 6,291,524 (Huang et al., issued Sep. 18, 2001); Hwu, J. R. et al. (1998); or McDonald, R. W. et al. (2001).

In one embodiment of the present invention, an NDGA derivative, tetra-O-methyl NDGA, also known as meso-1,4-bis(3,4-dimethoxyphenyl)-2,3-dimethylbutane, or $M_4N$ is made as follows: a solution is made containing NDGA and potassium hydroxide in methanol in a reaction flask. Dimethyl sulfate is then added to the reaction flask and the reaction is allowed to proceed. The reaction is finally quenched with water, causing the product to precipitate. The precipitate is isolated by filtration and dried in a vacuum oven. The compound is then dissolved in a solution of methylene chloride and toluene and subsequently purified through an alumina column. The solvents are removed by rotary evaporation and the solid is resuspended in isopropanol and isolated by filtration. The filter cake is dried in a vacuum oven. The resulting tetra-O-methyl NDGA ($M_4N$) is crystallized by refluxing the filter cake in isopropanol and re-isolating the crystals by filtration.

In some embodiments of the present invention, certain NDGA derivatives of the present invention, such as $G_4N$, also known as meso-1,4-bis[3,4-(dimethylaminoacetoxy)phenyl]-(2R,3S)-dimethylbutane or tetra-dimethylglycinyl NDGA, or a hydrochloride salt thereof and similar compounds having amino acid substituents, can also be prepared according to conventional methods, as described in, for example, U.S. Pat. No. 6,417,234.

Preparation of the Therapeutic Compositions

The present invention further provides compositions, including pharmaceutical compositions, comprising the catecholic butanes, including the NDGA derivatives, as active pharmaceutical ingredients ("API"), and pharmaceutically acceptable carriers or excipients. The API of the present invention can be incorporated into a variety of formulations for therapeutic administration, such as, for example, those described in PCT/US2004/016117, including nanoparticle formulations, micellar formulations, liposomal formulations, water-soluble formulations, or lipid-based formulations.

More particularly, the catecholic butanes of the present invention can be formulated into pharmaceutical compositions by combination with appropriate, pharmaceutically acceptable carriers, excipients or diluents, and may be formulated into solid, semi-solid, liquid, or gaseous forms, such as foams, sprays, film, pessaries, tablets, pills, capsules, sustained release formulations, powders, washes, liposomes, nanoparticles, granules, gels, creams, ointments, solutions, emulsions, suspensions, suppositories, injections, inhalants and aerosols. Pharmaceutically acceptable carriers or excipients suitable for use herein are described in a variety of publications. Examples of useful carriers or excipients are described in, for example, Gennaro, A. R. (2003); Ansel, H. C. et al. (2004); Rowe, R. C. et al. (2003); and Garg, S. et al. (2001).

The compositions herein are formulated in accordance to the mode of potential administration and the disease indication to be treated. Thus, if the composition is intended to be administered intranasally or by inhalation, for example, for the treatment of bronchial intraepithelial neoplasia, the composition may be a converted to a powder or spray in aerosol form, as conventional in the art, for such purposes. Other formulations, such as for oral or parenteral delivery, are also used as conventional in the art. Examples of the different formulations for treatment of different intraepithelial neoplasia via different routes of administration are set forth in Table 1.

TABLE 1

Routes of Administration for Different IEN
Oral and intravenous administration may be used for treatment of any of the intraepithelial neoplasia for early stage IEN (not clinically noticeable, but present) as well as for multiple lesions, or lesions not easily accessible to topical application, inhaled therapy, bladder instillation, rectal, intravaginal or other local therapy.

| Type of IEN | Tissue Type | Delivery |
|---|---|---|
| Gastrointestinal Tract | Oropharyngeal mucosal intraepithelial neoplasia | Oral Rinse, Oral Gel, Oral Adhesive gel, Oral mucosal patch, Oral Spray |
| | Esophageal intraepithelial neoplasia | Oral Tablet, Oral Liquid, Intravenous, Subcutaneous |
| | Pancreatic IN | Intravenous, Subcutaneous, Oral |
| | Duodenal, jejunal and colonic IN | Oral, intravenous, subcutaneous (low colonic may be suitable for foam, gel, enema) |
| Skin | Rectal | Suppository, foam, gel, enema |
| | Anal | Gel, cream, foam, suppository |
| | Actinic Keratosis (Pre-Squamos Cell Carcinoma), Pre- Basal Cell Carcinoma | Topical Cream, Lotion, Ointment, gel, Patch, spray. For more extensive cases, or for prophylaxis, oral, subcutaneous, intravenous |
| GenitoUrinary | Vaginal, Vulval, Cervical IN | Intravaginal gel, foam, liquid, cream, pessary |
| | Penile IN | Topical Gel, Cream, liquid, Oral |
| | Prostatic IN | Oral, Intravenous, Subcutaneous |
| | Bladder Mucosal Papillary TCC | Bladder Wash, Oral, Intravenous, Subcutaneous |
| | Bladder Mucosal transitional cell carcinoma in situ | Bladder Wash, Oral, Intravenous, Subcutaneous |
| | Testicular IN | Oral, Intravenous, Subcutaneous |
| Breast | Atypical Hyperplasia | Oral, Intravenous, Subcutaneous |
| | Ductal Intraepithelial Neoplasia | Oral, Intravenous, Subcutaneous |
| | Lobular Intraepithelial Neoplasia | Oral, Intravenous, Subcutaneous |
| Respiratory | Laryngeal IN | Oral, Intravenous, Subcutaneous |
| | Bronchial Intraepithelial Neoplasias (squamous and adenocarcinoma precursors) | Inhaled (spray, powder), Oral, Intravenous, Subcutaneous |
| Other | Conjunctival-Corneal IN | Topical Ocular Drops, Oral |

The compositions in liquid form may include a buffer, which is selected according to the desired use of the catecholic butanes or NDGA derivatives, and may also include other substances appropriate for the intended use. Those skilled in the art can readily select an appropriate buffer, a wide variety of which are known in the art, suitable for an intended use. In some instances, the composition can comprise a pharmaceutically acceptable excipient, a variety of which are known in the art.

Typically, the compositions of the instant invention will contain from less than about 0.5% up to about 99% of the active pharmaceutical ingredient or API, that is, the catecholic butanes, including the NDGA derivatives herein; optionally, the instant invention will contain about 2% to about 90% of the active ingredient.

The present pharmaceutical composition includes the active ingredient or API being present in the composition at a concentration in a range, for example, where the compound is for application onto the surface of the neoplasia or for delivery by inhalation, by intranasal administration, or as a rinse or a wash, or as a suppository or an enema, of about 0.5 wt % to about or less than about 50 wt %, or less than 40 wt %, or less than 30 wt %, optionally, the concentration of the compound is about or less than about 27.5 wt %, or 25 wt %, or 22.5 wt %, or 20 wt %, or 17.5 wt %, or 15 wt %, or 12.5 wt %, or 10 wt %, or 7.5 wt %, or 5 wt %, or 2 wt %, or 1.25 wt %.

Where, for example the pharmaceutical composition is for administration intravenously, intraperitoneally, or subcutaneously, the API is present in the composition at a concentration in a range of about 0.1 mg/ml to about or less than about 500 mg/ml, optionally, the concentration is in a range of about 0.5 mg/ml to about or less than 475 mg/ml, or about 1 mg/ml to about or less than 400 mg/ml, or about 2 mg/ml to about or less than 375 mg/ml, or about 5 mg/ml to about or less than 350 mg/ml, or about 7.5 mg/ml to about or less than 325 mg/ml, or about 10 mg/ml to about or less than 300 mg/ml, or about 12.5 mg/ml to about or less than 275 mg/ml, or about 15 mg/ml to about or less than 250 mg/ml, or about 17.5 mg/ml to about or less than 225 mg/ml, or about 20 mg/ml to about or less than 200 mg/ml, or about 25 mg/ml to about or less than 175 mg/ml, or about 50 mg/ml to about or less than 150 mg/ml, or about 75 mg/ml to about or less than 125 mg/ml, or about 90 mg/ml to about or less than 120 mg/ml.

Where the pharmaceutical composition is for administration orally, for example, as a tablet, the API is present in the composition at a concentration of not less than about 98 wt %, or about 95 wt %, or about 90 wt %, or 80 wt %, or 70 wt %, or 60 wt %, or 50 wt %, or 40 wt %, or 30 wt %, or 20 wt %, or 10 wt %, or 5 wt %, or about 2 wt %, or about 1 wt %.

For example, in one embodiment, the present composition is formulated as a jelly and includes, one or more of glacial acetic acid, oxyquinoline sulfate, ricinoleic acid, glycerin, tragacanth, acacia, propyl paraben, potassium hydroxide, stannous chloride, potassium bitartarate, and water, and optionally egg albumin or fragrance or perfume. In another embodiment, the jelly includes, for example, any of the foregoing or one or more of lactic acid, methyl paraben, povidone, propylene glycol, sodium carboxymethyl cellulose, sorbic acid and sorbitol solution. In a further embodiment, the jelly includes, for example, any of the foregoing or one or more of boric acid and cellulose gum. In yet another embodiment, the jelly includes, for example, any of the foregoing or one or more of Cremaphor and hydroxyethyl cellulose.

For example, in another embodiment of the present invention, the composition is formulated as a bioadhesive gel. For example, such a gel includes one or more of water, glycerin, mineral oil, Polycarobphil, hydrogenated palm oil glyceride, Carbomer 934P, methyl paraben, sorbic acid and NaOH.

For example, in a further embodiment, the present composition is formulated as a gel and includes one or more of Carbopol 974P, or one or more of C31 G, type A gelatin, purified corn starch, hydroxypropylmethyl cellulose, glycerin/glycerine and water. In one aspect of the invention, the gel includes any of the foregoing or one or more of cellulose gum, lactic acid, methyl paraben, povidone, propylene glycol, sorbic acid and sorbitol solution. In another aspect of the invention, the gel includes any of the foregoing or one or more of mineral oil, Polycarobphil, Carbomer 934P, hydrogenated palm oil glyceride and sodium hydroxide. In yet another aspect of the invention, the gel includes any of the foregoing or one or more of EDTA and propyl paraben. In yet another aspect of the invention, the gel includes any of the foregoing or one or more of colloidal silicon dioxide and triacetin.

In another embodiment of the invention, the present composition is formulated as a cream and the cream includes, for example, one or more of urea, sodium propionate, methionine, cysteine and inositol. In another embodiment, the cream includes any of the foregoing or one or more of lactose, propylene glycol, stearic acid, diglycol stearate, methyl paraben, propyl paraben, trolamine and lactic acid. In yet another embodiment, the cream includes any of the foregoing or one or more of benzyl alcohol, cetyl alcohol, 1-octyl dodecanol, polysorbate 60, sorbitan monostearate and spermaceti. In another aspect of the invention, the cream includes any of the foregoing or one or more of cetostearyl alcohol, cetyl palmitate and mineral oil. In yet another aspect, the cream includes any of the foregoing or one or more of sodium phosphate, monobasic adipic acid, colloidal silicon dioxide, magnesium stearate, maize starch, polysorbate 80, and sodium bicarbonate. In still another aspect, the cream includes any of the foregoing or one or more of aloe barbadensis gel, aluminium sulfate, calcium acetate, cetearyl alcohol, corn oil, glycerine, isopropyl palmitate, light mineral oil, maltodextrin, potato dextrin, water, sodium cetearyl sulfate, sodium lauryl sulfate, vitamin A palmitate, vitamin D, vitamin E, white petrolatum, and white wax. In a further aspect, the cream includes any of the foregoing or one or more of benzoic acid, butylated hydroxyl anisole, fragrance, palm oil and Peg stearate. In another aspect, the cream includes any of the foregoing or one or more of stearyl alcohol, white ceresin wax, glyceryl stearate or monostearate, and hydroxypropylmethyl cellulose. In another aspect, the cream includes any of the foregoing or one or more of propylene glycol 100 stearate, cetyl esters wax, Peglicol 5 oleate, Pegoxol stearate, propylene glycol 400 stearate, cetyl stearyl alcohol, peanut oil, glycerin, glutamic acid, citric acid, sodium hydroxide, propylene glycol monostearate, methyl stearate, SLS, cholesterol, diethylaminoethyl stearamide, lanolin, lecithin, phosphoric acid, isopropyl myristate, and propyl glycol.

In another embodiment of the invention, the composition is formulated as a suppository and the suppository contains, for example, one or more of propylene glycol 400 and 3350, polysorbate 80, glycerin, lactic acid, cover made of gelatin, water, methyl paraben, propyl paraben, and color. In another aspect of the invention, the suppository includes any of the foregoing or one or more of C31G, and propylene glycol 1450 or 8000. In another aspect, the suppository includes any of the foregoing or one or more of sodium bicarbonate, sodium citrate, and tartaric acid or glycerides of fatty acids, or butylated hydroxyl anisole, palm kernel oil and coconut oil.

In another embodiment of the invention, the composition is formulated as a tablet and the tablet contains, for example, one or more of adipic acid, colloidal silicon dioxide, lactose, magnesium stearate, maize starch, Polysorbate 80, sodium bicarbonate, and stearic acid. In another embodiment, the tablet comprises any of the foregoing or one or more of microcrystalline cellulose, hydroxypropylmethyl cellulose, lactic acid and crospovidone. In yet another aspect, the tablet contains any of the foregoing or one or more of potato starch, gelatin, and talc.

In yet another embodiment of the invention, the composition is formulated as a douche and the douche contains, for example, one or more of sodium citrate, citric acid, vinegar, O-9, diazolidinyl urea, cetylpyridinium chloride, EDTA, SD alcohol 40 and water.

In another embodiment, the composition is provided on a film and the film contains, for example, one or more of glycerine and polyvinyl alcohol.

Examples of different formulations are set forth in Table 2.

TABLE 2

Formulation for the present pharmaceutical compositions.

| DOSAGE FORM | COMPOSITION |
| --- | --- |
| Jelly | Glacial acetic acid, oxyquinoline sulfate, ricinoleic acid, glycerin, tragacanth, acacia, propyl paraben, potassium hydroxide, stannous chloride, egg albumin, potassium bitartarate, perfume, water |
| | Lactic acid, methyl paraben, povidone, propylene glycol, water, sodium carboxymethyl cellulose, sorbic acid, sorbitol solution |
| | Boric acid, cellulose gum, fragrance, propylene glycol |
| | Cremaphor, hydroxyethyl cellulose, methyl paraben, propylene glycol, water, sorbic acid |
| Gel or Bioadhesive Gel | Water, glycerin, mineral oil, Polycarbophil, hydrogenated palm oil glyceride, Carbomer 934P, methyl paraben, sorbic acid, NaOH |
| | Carbopol 974P |
| | C31G (as a 10% concentrate), type A gelatin, purified corn starch, hydroxypropylmethyl cellulose, glycerine, water |
| | Cellulose gum, lactic acid, methyl paraben, povidone, propylene glycol, water, sorbic acid, sorbitol solution |
| | Glycerine, mineral oil, Polycarbophil, Carbomer 934P, hydrogenated palm oil glyceride, sorbic acid, NaOH |
| | Carbomer 934P, EDTA, methyl paraben, propyl paraben, propylene glycol, NaOH |
| | Colloidal silicon dioxide, triacetin |
| | Glycerin, mineral oil, Polycarbophil, hydrogenated palm oil glyceride, Carbomer 934P, methyl paraben, sorbic acid, NaOH, $H_2O$ |
| Cream | Urea, sodium propionate, methionine, cysteine, inositol |
| | Lactose, propylene glycol, stearic acid, diglycol stearate, methyl paraben, propyl paraben, trolamine, lactic acid. |
| | Benzyl alcohol, cetyl stearyl alcohol, 1-oaty dodecanol, Polysorbate 60, water, sorbitan monostearate, spermaceti |
| | Benzyl alcohol, cetostearyl alcohol, cetyl palmitate, mineral oil, Polysorbate 60, propylene glycol, sorbitan monostearate, stearic acid |
| | Sodium phosphate, monobasic, adipic acid, colloidal silicon dioxide, lactose, magnesium stearate, maize starch, Polysorbate 80, sodium bicarbonate, stearic acid |
| | Aloe barbadensis gel, aluminium sulfate, calcium acetate, cetearyl alcohol, cetyl alcohol, corn oil, glycerine, isopropyl palmitate, light mineral oil, maltodextrin, methyl paraben, potato dextrin, propylene glycol, propyl paraben, water, sodium cetearyl sulfate, sodium lauryl sulfate, vitamin A palmitate, Vitamin D and E, white petrolatum, white wax |
| | Benzoic acid, butylated hydroxyl anisole, mineral oil, fragrance, palm oil, polyethylene glycol, Peg stearate |
| | Propylene glycol, stearyl alcohol, white ceresin wax, glyceryl monostearate, hydroxypropylmethyl cellulose |
| | Cetyl alcohol, glyceryl stearate, propylene glycol 100 stearate, methyl paraben, propyl paraben, mineral oil, Polysorbate 60, propylene glycol, sorbitan monostearate, stearyl alcohol, $H_2O$ |
| Ointment | White petrolatum, benzyl alcohol, propylene glycol, water, SD alcohol |
| | Aluminium magnesium silicate, butylated hydroxyl anisole, white soft paraffin |
| Tablet | Adipic acid, colloidal silicon dioxide, lactose, magnesium stearate, maize starch, Polysorbate 80, sodium bicarbonate, stearic acid |
| | Colloidal silicon dioxide, potato starch, gelatin, magnesium stearate, talc, corn starch, lactose |
| | Lactose, macrocrystalline cellulose, hydroxypropylmethyl cellulose, silicon dioxide, magnesium stearate, corn starch, lactic acid, crospovidone |
| Suppository | Polyethylene glycol 400 and 3350, Polysorbate 80, glycerin, lactic acid, cover made up of gelatin, glycerin, water, methyl paraben, propyl paraben, color |
| | C31G (as a 10% concentrate), polyethylene glycol 400, 1450, 3350, 8000 |
| | Glycerides of fatty acids |
| | Butylated hydroxyl anisole, palm kernel oil, coconut oil, glycerides |
| Films | Glycerine, polyvinyl alcohol |
| Foam | Benzoic acid, cellulose gum, cetyl alcohol, glacial acetic acid, methyl paraben, perfume, phosphoric acid, polyvinyl alcohol, propellant A31, propylene glycol, water, sorbic acid, searamidoehtyl diethylamine, stearic acid |
| Douche | Sodium citrate, citric acid, vinegar, O-9, diazolidinyl urea, cetylpyridinium chloride, EDTA, SD alcohol 40, water |

Therapeutic Methods

The catecholic butanes, including the NDGA derivatives of the subject invention find use as therapeutic agents in situations where one wishes to provide a treatment to a subject who has intraepithelial neoplasia or dysplasia.

A variety of animal hosts are treatable according to the subject methods, including human and non-human animals. Generally such hosts are "mammals" or "mammalian," where these terms are used broadly to describe organisms which are within the class mammalia, including the orders carnivore (e.g., dogs and cats), rodentia (e.g., guinea pigs, and rats), and other mammals, including cattle, goats, horses, sheep, rabbits, pigs, and primates (e.g., humans, chimpanzees, and monkeys). In many embodiments, the hosts will be humans. Animal models are of interest for experimental investigations, such as providing a model for treatment of human disease. Further, the present invention is applicable to veterinary care as well.

Formulations, Dosages, and Routes of Administration

In one embodiment of the invention, an effective amount of the present composition is administered to the host, where an "effective amount" means a dosage sufficient to produce a desired result. In some embodiments, the desired result is at least an inhibition of progression of the neoplasia or dysplasia.

The appropriate dose to be administered depends on the subject to be treated, such as the general health of the subject, the age of the subject, the state of the disease or condition, the weight of the subject, the size of the tumor, for example. Generally, between about 0.1 mg and about 500 mg or less may be administered to a child and between about 0.1 mg and about 5 grams or less may be administered to an adult. The active agent can be administered in a single or, more typically, multiple doses. Preferred dosages for a given agent are readily determinable by those of skill in the art by a variety of means. Other effective dosages can be readily determined by one of ordinary skill in the art through routine trials establishing dose response curves. The amount of agent will, of course, vary depending upon the particular agent used.

In one embodiment of the invention, the composition is administered to the subject with the API being at a dose in the range of about 0.5 mg/kg to about or less than about 300 mg/kg, or about 1 mg/kg to about or less than about 275 mg/kg, or about 5 mg/kg to about or less than 250 mg/kg, or about 7.5 mg/kg to about or less than 225 mg/kg, or about 10 mg/kg to about or less than 200 mg/kg, or about 25 mg/kg to about or less than 175 mg/kg, or about 50 mg/kg to about or less than 150 mg/kg, or about 75 mg/kg to about or less than 125 mg/kg, or about 90 mg/kg to about or less than 100 mg/kg.

In another embodiment, the composition is administered to the subject with the API being at a dose in the range of about 0.5 mg/cm$^2$ on the basis of the size of the neoplasia, to about or less than about 300 mg/cm$^2$, or about 1 mg/cm$^2$ to about or less than about 275 mg/cm$^2$, or about 5 mg/cm$^2$ to about or less than 250 mg/cm$^2$, or about 7.5 mg/cm$^2$ to about or less than 225 mg/cm$^2$, or about 10 mg/cm$^2$ to about or less than 200 mg/cm$^2$, or about 25 mg/cm$^2$ to about or less than 175 mg/cm$^2$, or about 50 mg/cm$^2$ to about or less than 150 mg/cm$^2$, or about 75 mg/cm$^2$ to about or less than 125 mg/cm$^2$, or about 90 mg/cm$^2$ to about or less than 100 mg/cm$^2$.

The frequency of administration of the active agent, as with the doses, will be determined by the care giver based on age, weight, disease status, health status and patient responsiveness. Thus, the agents may be administered one or more times daily, weekly, monthly or as appropriate as conventionally determined. The agents may be administered intermittently, such as for a period of days, weeks or months, then not again until some time has passed, such as 3 or 6 months, and then administered again for a period of days, weeks, or months.

Administration of the active agents can be achieved in various ways, such as by oral, buccal, rectal, intranasal, intravenous, subcutaneous, intraperitoneal, intra-arterial, intratracheal, intraventricular, intracranial, interstitial, transdermal, etc., or by inhalation or implantation such as in pessaries and suppositories.

Further as an example, nanoparticle, micelle and liposomal preparations containing the present API can be prepared as described in PCT/US2004/016117 and administered systemically, including parenterally and intranasally, as well as interstitially, orally, topically, transdermally, via inhalation or implantation, such as for drug targeting, enhancement of drug bioavailability and protection of drug bioactivity and stability. Nanoparticle bound drugs herein are expected to achieve prolonged drug retention in tumors.

In pharmaceutical dosage forms, the active agents may be administered in the form of their pharmaceutically acceptable salts, or they may also be used alone or in appropriate association, as well as in combination, with other pharmaceutically active agents or therapeutics including other small molecules, antibodies or protein therapeutics. The following methods and excipients are merely exemplary and are in no way limiting.

For oral preparations, the active agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents. For oral rinses, the preparations can be made in a manner conventional in the art, such as described in, for example, Epstein, J. B. et al. (2002) and Pitten, F. et al. (2003).

In addition, if desired, the carrier or excipient may contain minor amounts of auxiliary substances such as pH adjusting and buffering agents, tonicity adjusting agents, stabilizers, wetting agents or emulsifying agents. Actual methods of preparing such dosage forms are known, or will be apparent, to those skilled in the art. See, e.g., Remington's Pharmaceutical Sciences, 20th ed., Mack Publishing Co. Rawlins EA, (1997). The composition or formulation to be administered will, in any event, contain a quantity of the API adequate to achieve the desired state in the subject being treated.

The active agents can be formulated into preparations for injection by dissolving, suspending or emulsifying them in an aqueous or non-aqueous solvent, such as vegetable or other similar oils, including corn oil, castor oil, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The active agents can be utilized in aerosol formulation to be administered via inhalation. The compounds of the present invention can be formulated into pressurized acceptable propellants such as dichlorodifluoromethane, propane, nitrogen and the like.

Furthermore, the active agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the API. Similarly, unit dosage forms for injection or intravenous administration may comprise the API in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of API of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

Kits with multiple or unit doses of the active agent, are included in the present invention. In such kits, in addition to the containers containing the multiple or unit doses of the compositions containing the NDGA derivatives will be an informational package insert with instructions describing the use and attendant benefits of the drugs in treating pathological condition of interest. Optionally, an applicator for administration of the present composition is included in each kit.

INDUSTRIAL APPLICABILITY

The compositions and formulations described herein are useful for the treatment of intraepithelial neoplasia or dysplasia, such as, for example, mucosal, cervical, prostatic, penile, testicular, vulvar, oral, anal, pancreatic, lung, breast, colon, colorectal, head and neck, esophageal, conjunctival-corneal, or bladder intraepithelial neoplasia or dysplasia, with our without association with viral infections, such as HIV, HPV, HSV, HBV, HCV, EBV, JC virus, Varicella-zoster virus, adenovirus, parvovirus or lentivirus.

The Examples set forth below are exemplary in nature and are not to be interpreted as limiting the present invention.

Example 1

Cervical Application of M4N

Fourteen Day Rabbit Intravaginal Topical Toxicology Study. This study was designed to look at the local and systemic toxicity of tetra-O-methyl NDGA ($M_4N$) administered intravaginally in New Zealand White rabbits for 14 days. Rabbits were dosed daily with 1 mL of a white petrolatum formulation of $M_4N$ (20 mg/g) or placebo. Ten female rabbits (5 per group) were dosed. Local effects of drug were scored using the Draize scoring system daily, and gross pathology and histopathology was obtained at necropsy on termination of the dosing period.

All animals survived until scheduled termination. No findings were noted on weekly clinical, and twice daily cage-side observations. Vaginal observations were limited to minimal edema in 2/5 control animals, and minimal edema, mild edema, and mild erythema in 1/5, 2/5 and 3/5 $M_4N$ treated animals respectively, attributed to be likely to be due to dosing procedure. In one rabbit, inflammation of the urinary bladder was noted, and in one $M_4N$-treated rabbit, heterophil infiltrates were seen in the vaginal mucosa. It is unknown if these findings were drug related, or related to the dosing procedure. There were no other treatment related histologic or gross organ changes, and findings of lower absolute basophil counts, and ALT values in the $M_4N$-treated group were considered incidental. Minimal absorption of $M_4N$ occurred after administration, with serum levels inconsistent, and generally less than 10 ng/mL at peak concentration. It was concluded that administration of $M_4N$ in white petrolatum for 14 days as an intravaginal application produced incidental minimal or mild edema in both control and $M_4N$-treated rabbits, and minimal erythema in $M_4N$-treated rabbits. There were single instances of inflammation in the urinary bladder and heterophilic infiltrates transmigrating the vaginal mucosa into the lumen in treated rabbits which are most likely related to dosing procedure.

Example 2

Inhibition of SP1-Binding Activity

Inhibition of Sp-1 binding activity can be determined by any conventional method, for example, in a gel mobility shift assay as described in U.S. Pat. No. 6,608,108. Briefly, different concentrations of the present compounds, such as $M_4N$ in DMSO or $G_4N$ (tetra-O—N,N-dimethylglycinyl NDGA) in PBS can be incubated with $^{32}P$-labeled DNA in a binding buffer for 30 min at 25° C. DNA binding domain of recombinant Sp1 protein (Sp1-167D) can be next added and incubated for additional 30 min in the presence of a large excess of BSA protein. The gels can be 5% non-denaturing polyacrylamide gel with each lane being loaded with 5 µl of each reaction volume.

Example 3

Solubility of $M_4N$ in Water-Insoluble Lipids

A 2 g mixture of $M_4N$ at a concentration of about 200 mg/g in 85% olive oil and 15% beeswax was made as follows. About 1.7 ml of olive oil was added to a glass beaker containing a stir bar. The beaker was placed on a magnetic plate and the stir bar was set to stir at medium speed. About 400 mg of $M_4N$ was slowly added to the olive oil in the center of the beaker with the aid of a spatula to prevent $M_4N$ from sticking to the beaker wall. The $M_4N$/olive oil mixture was stirred for about 2 hr or until all $M_4N$ had dissolved or was uniformly suspended without any clump being present. The $M_4N$/olive oil mixture was optionally heated at about 60° C. for about 30 min. (or longer if a larger volume of solution was desired, for example, 1 hr at 60° C. for 100 ml of the $M_4N$/olive oil mixture), or longer as need to ensure complete dissolution of $M_4N$. The $M_4N$/olive oil mixture was observed for presence of any undissolved $M_4N$ by holding the beaker against a white followed by a dark background, looking for presence of particulates. If crystals formed, the $M_4N$/olive oil solution could be heated again at 60° C. for about 1 hr, with stirring, on a hot magnetic plate until all $M_4N$ was dissolved back in solution. About 300 mg of white beeswax was added to a glass beaker containing a stir bar. The beaker was also placed on a magnetic plate and the stir bar was set to stir at medium speed. The beeswax was heated at about 50° C. for about 30 min. (or longer if a larger quantity was desired), or until all the beeswax was melted. The $M_4N$/olive oil solution was then added to about 300 mg of melted beeswax and stirred and heated at about 50° C. for about 30 min or until all the $M_4N$/olive oil/beeswax mixture had dissolved or was uniformly mixed. The stir bar was removed from the beaker and the $M_4N$/olive oil/beeswax mixture was allowed to cool down. The final $M_4N$/olive oil/beeswax mixture was stored at room temperature and was kept protected from light. This process may be scaled up or down to obtain the requisite volume or concentration of $M_4N$. This process formed a yellow cream with a melting point of 40° C. Formulations containing $M_4N$ in other water-insoluble lipids may be similarly made, such as, for example, by substituting olive oil in the process described above with mineral oil, corn oil, sesame oil, soybean oil, peppermint oil, lecithin, or other solubilizing agents, and combinations thereof, and substituting beeswax with paraffin, PEG 3350, or other stiffening agents, and combinations thereof.

A 2 g mixture of $M_4N$ at a concentration of about 200 mg/g (w/w) in 70% olive oil, 15% beeswax and 15% lecithin was made as follows. About 1.4 ml of olive oil was added to a glass beaker containing a stir bar. The beaker was placed on a magnetic plate and the stir bar was set to stir at medium speed. About 400 mg of $M_4N$ was slowly added to the olive oil in the center of the beaker with the aid of a spatula to prevent $M_4N$ from sticking to the beaker wall. The $M_4N$/olive oil mixture was stirred for about 2 hr or until all $M_4N$ had dissolved or was uniformly suspended without any clump being present. The $M_4N$/olive oil mixture was optionally heated at about 60° C. for about 30 min. (or longer if a larger volume of solution was desired, for example, 1 hr at 60° C. for 100 ml of the $M_4N$/olive oil mixture), or longer as need to ensure complete dissolution of $M_4N$. The $M_4N$/olive oil mixture was observed for presence of any undissolved $M_4N$ by holding the beaker against a white followed by a dark background, looking for presence of particulates. If crystals formed, the $M_4N$/olive oil solution could be heated again at 60° C. for about 1 hr, with stirring, on a hot magnetic plate until all $M_4N$ was dissolved back in solution. About 300 mg of white beeswax and about 300 mg of lecithin were added to a glass beaker containing a stir bar. The beaker was also placed on a magnetic plate and the stir bar was set to stir at medium speed. The beeswax/lecithin mixture was heated at about 50° C. for about 30 min. (or longer if a larger quantity was desired), or until all the beeswax and lecithin were melted. The $M_4N$/olive oil solution was then added to about 600 mg of melted beeswax/lecithin mixture and stirred and heated at about 50° C. for about 30 min or until all the $M_4N$/olive oil/beeswax mixture had dissolved or was uniformly mixed. The stir bar was removed from the beaker and the $M_4N$/olive oil/beeswax/lecithin mixture was allowed to cool down. The final $M_4N$/olive oil/beeswax/lecithin mixture was stored at room temperature and was kept protected from light. This process may be scaled up or down to obtain the requisite volume or concentration of $M_4N$. This process formed a yellow cream with a melting point of about 37° C. Formulations containing $M_4N$ in other water-insoluble lipids may be similarly made, such as, for example, by substituting olive oil in the process described above with mineral oil, corn oil, sesame oil, soybean oil, peppermint oil, or other solubilizing agents, and combinations thereof, substituting beeswax with paraffin, PEG 3350, or other stiffening agents, and combinations thereof, and substituting lecithin with Tween 80, TPGS, Tween 20, PEG 300, PEG 400, PEG 400 monolaurate, glycerol, polyvinyl pyrrolidone, propylene glycol, or other solubilizing agents, and combinations thereof.

Formulations containing $M_4N$ in other water-insoluble lipids combined with non-ionic, ionic or amphipathic surfactants or water-soluble organic solvents may be similarly made, such as, for example, by substituting olive oil in the process described above with corn oil, sesame oil, soybean oil, peppermint oil, or mineral oil, substituting lecithin with Tween 80, TPGS, Tween 20, PEG 300, PEG 400, PEG 400 monolaurate, glycerol, polyvinyl pyrrolidone, propylene glycol, or other solubilizing agents, and combinations thereof, and substituting white beeswax with paraffin, PEG 3350, or other stiffening agents, and combinations thereof.

Example 4

Solubility of $M_4N$ in Water-Soluble Organic Solvents

A 2 g mixture of $M_4N$ at a concentration of about 200 mg/g (w/w) in 40% PEG 400, 40% Tween 80 and 20% PEG3350 was made as follows. About 0.8 ml of PEG 400 and about 0.8 ml of Tween 80 were added to a glass beaker containing a stir bar. The beaker was placed on a magnetic plate and the stir bar was set to stir at medium speed. About 400 mg of $M_4N$ was slowly added to the PEG400/Tween80 mixture in the center of the beaker with the aid of a spatula to prevent $M_4N$ from sticking to the beaker wall. The $M_4N$/PEG400/Tween80 mixture was stirred for about 2 hr or until all $M_4N$ had dissolved or was uniformly suspended without any clump being present. The $M_4N$/PEG400/Tween80 mixture was optionally heated at about 60° C. for about 30 min. (or longer if a larger volume of solution was desired, for example, 1 hr at 60° C. for 100 ml of the $M_4N$/PEG400/Tween80 mixture), or longer as need to ensure complete dissolution of $M_4N$. The $M_4N$/PEG400/Tween80 mixture was observed for presence of any undissolved $M_4N$ by holding the beaker against a white followed by a dark background, looking for presence of particulates. If crystals formed, the $M_4N$/PEG400/Tween80 solution could be heated again at 60° C. for about 1 hr, with stirring, on a hot magnetic plate until all $M_4N$ was dissolved back in solution. About 400 mg of PEG 3350 was added to a glass beaker containing a stir bar. The beaker was also placed on a magnetic plate and the stir bar was set to stir at medium speed. The PEG3350 was heated at about 50° C. for about 30 min. (or longer if a larger quantity was desired), or until all the PEG 3350 was melted. The $M_4N$/PEG400/Tween80 solution was then added to about 400 mg of melted PEG3350 and stirred and heated at about 55° C. for about 30 min or until all the $M_4N$/PEG400/Tween80/PEG3350 mixture had dissolved or was uniformly mixed. The stir bar was removed from the beaker and the $M_4N$/PEG400/Tween80/PEG3350 mixture was allowed to cool down. The final $M_4N$/PEG400/Tween80/PEG3350 mixture was stored at room temperature and was kept protected from light. This process may be scaled up or down to obtain the requisite volume or concentration of $M_4N$. This process formed a smooth white cream with a melting point of about 38.5° C. Formulations containing $M_4N$ in other water-soluble organic solvents or surfactants may be similarly made, such as, for example, by substituting PEG 400 and/or Tween 80 in the process described above with Tween 20, Tween 80, TPGS, lecithin, PEG 300, PEG 400, PEG 400 monolaurate, glycerol, polyvinyl pyrrolidone, propylene glycol, or other solubilizing agents, and combinations thereof, substituting PEG 3350 with paraffin, beeswax or other stiffening agents, and combinations thereof.

Example 5

Solubility of $M_4N$ in Surfactants

A 2 g mixture of $M_4N$ at a concentration of about 200 mg/g (w/w) in 45% Tween 80, 40% PEG 400, 7.5% beeswax and 7.5% PEG3350 was made as follows. About 0.9 ml of Tween 80 and about 0.8 ml of PEG 400 were added to a glass beaker containing a stir bar. The beaker was placed on a magnetic plate and the stir bar was set to stir at medium speed. About 400 mg of M$_4$N was slowly added to the Tween80/PEG400 mixture in the center of the beaker with the aid of a spatula to prevent M$_4$N from sticking to the beaker wall. The M$_4$N/Tween80/PEG400 mixture was stirred for about 2 hr or until all M$_4$N had dissolved or was uniformly suspended without any clump being present. The M$_4$N/Tween80/PEG400 mixture was optionally heated at about 60° C. for about 30 min. (or longer if a larger volume of solution was desired, for example, 1 hr at 60° C. for 100 ml of the M$_4$N/Tween80/PEG400 mixture), or longer as need to ensure complete dissolution of M$_4$N. The M$_4$N/Tween80/PEG400 mixture was observed for presence of any undissolved M$_4$N by holding the beaker against a white followed by a dark background, looking for presence of particulates. If crystals formed, the M$_4$N/Tween80/PEG400 solution could be heated again at 60° C. for about 1 hr, with stirring, on a hot magnetic plate until all M$_4$N was dissolved back in solution. About 150 mg of white beeswax and about 150 mg of PEG 3350 were added to a glass beaker containing a stir bar. The beaker was also placed on a magnetic plate and the stir bar was set to stir at medium speed. The beeswax/PEG3350 mixture was heated at about 50° C. for about 30 min. (or longer if a larger quantity was desired), or until all the beeswax and PEG 3350 were melted. The M$_4$N/Tween80/PEG400 solution was then added to about 600 mg of melted beeswax/PEG3350 mixture and stirred and heated at about 50° C. for about 30 min or until all the M$_4$N/Tween80/PEG400/beeswax/PEG3350 mixture had dissolved or was uniformly mixed. The stir bar was removed from the beaker and the M$_4$N/Tween80/PEG400/beeswax/PEG3350 mixture was allowed to cool down. The final M$_4$N/Tween80/PEG400/beeswax/PEG3350 mixture was stored at room temperature and was kept protected from light. This process may be scaled up or down to obtain the requisite volume or concentration of M$_4$N. This process formed a smooth white cream with a melting point of about 37.5° C. Formulations containing M$_4$N in other water-soluble organic solvents or surfactants may be similarly made, such as, for example, by substituting PEG 400 and/or Tween 80 in the process described above with Tween 20, Tween 80, TPGS, lecithin, PEG 300, PEG 400, PEG 400 monolaurate, glycerol, polyvinyl pyrrolidone, propylene glycol, or other solubilizing agents, and combinations thereof, substituting beeswax and/or PEG 3350 with paraffin, PEG 3350, beeswax or other stiffening agents, and combinations thereof.

Example 6

Clinical Cervical Application of M4N

A Pilot Translational Clinical Trial of Tetra-O-Methyl Nordihyrdroguaiaretic Acid (M4N) for the Treatment of Cervical Intraepithelial Neoplasia This study was designed to look at the systemic and local toxicity of tetra-O-methyl NDGA (M4N) administered intravaginally to women once a week for three weeks. Patients, at the time of screening, had visible cervical lesions, were HPV positive, and had previous biopsy confirmed Cervical Intraepithelial Neoplasia (CIN). Cervical biopsies were taken at Day 1 and follow up biopsies were taken at Day 71. Five patients have been enrolled in the study, and three patients have completed the study through Day 71.

The first four patients received 5 mL of a 1% formulation of M4N in white petrolatum once weekly for each of three weekly doses. No irritation or toxicity was reported after any of the 1% M4N administrations. One patient received 5 mL of a 2% M4N formulation in white petrolatum at each of two weekly doses to date. No vaginal irritation or toxicity was reported after the 2% M4N administrations, however minor vulvar irritation was reported after each of the 2% administrations. The relationship to the study drug administration is unknown.

Serum levels were below limit of quantification after administration of the 1% formulation.

Preliminary efficacy data was collected from cervical biopsies at Day 1 and Day 71 from the three patients that completed the Day 71 visit after receiving 3 doses of the 1% formulation of M4N. The biopsies indicated that one patient had a complete response, one patient had a partial response, and one patient showed disease progression.

Example 7

Cervical Application of M4N

Intravaginal Irritation and Pharmacokinetics Study of M4N in Rabbits

This study was designed to investigate absorption and irritation of M4N formulated in different excipient combinations administered intravaginally in New Zealand White rabbits for 5 days. Thirty New Zealand White rabbits were randomly assigned to six dosage groups (Groups I through VI), five rabbits per group. Formulations of M4N (20% M4N in different excipient combinations, 200 mg/mL) were administered intravaginally once daily to these rabbits on days 1 through 5 of study (DSs 1 through 5) at 50 mg/kg/day. The dosage volume was 0.25 mL/kg, adjusted daily on the basis of the individual body weights recorded immediately before administration. Blood samples were collected on DSs 1 and 5 from each rabbit prior to dosage and at approximately 30 minutes, 1, 2, 4 and 8 hours postdosage. Local effects of drug were scored using the Draize scoring system daily, and gross pathology was obtained at necropsy on termination of the dosing period.

One doe administered 50 mg/kg/day M4N in olive oil and white beeswax was found dead on day five of the study (DS 5). It was not believed that this single death was related to the test article. All other does survived to scheduled sacrifice. No adverse clinical observations attributed to M4N in any vehicle (excluding vaginal scoring) occurred in any of the groups. Body weights and body weight gains (losses) were comparable among the groups. In surviving does, with the exception of a white or yellow viscous material (attributed to be test material), no necropsy observation occurred in more than a single doe in any group. These singular animal findings included a white viscous material in the caudal region of the vagina, numerous red areas at the urinary meatus (cranial region), soft white material in the cranial to caudal region of the vagina (to the urinary meatus), a dark red serosal surface at the distal end of the vagina, a mass at the urinary meatus and soft white material in the bladder. White or yellow material in the cranial region of the vagina was observed in one to three does in all groups, except the white petrolatum group.

Scoring of possible vaginal irritation was conducted daily beginning immediately before the first dosage, prior to each daily dosage administration and approximately 4 hours postdosage. White petrolatum appeared to cause the least amount of vaginal irritation (erythema and/or edema, grades 1 or 2) or vaginal discharge of all the vehicles. Although none of the other vehicles were very irritating, the most to least irritating vehicles based on erythema and edema appeared to be: 1) Polysorbate 80, PEG 400 and PEG 3350; 2) olive oil, white beeswax and lecithin; 3) Polysorbate 80, PEG 400, white beeswax group and PEG 3350; 4) olive oil and white beeswax group and 5) mineral oil and white beeswax group. Vaginal discharge, generally slight, occurred most often in the mineral oil and white beeswax; followed by the Polysorbate 80, PEG 400, white beeswax and PEG 3350; and olive oil, white beeswax in lecithin groups. No other adverse clinical or necropsy observations related to M4N in any vehicle (excluding vaginal scoring) occurred in any of the groups.

Figure 1:
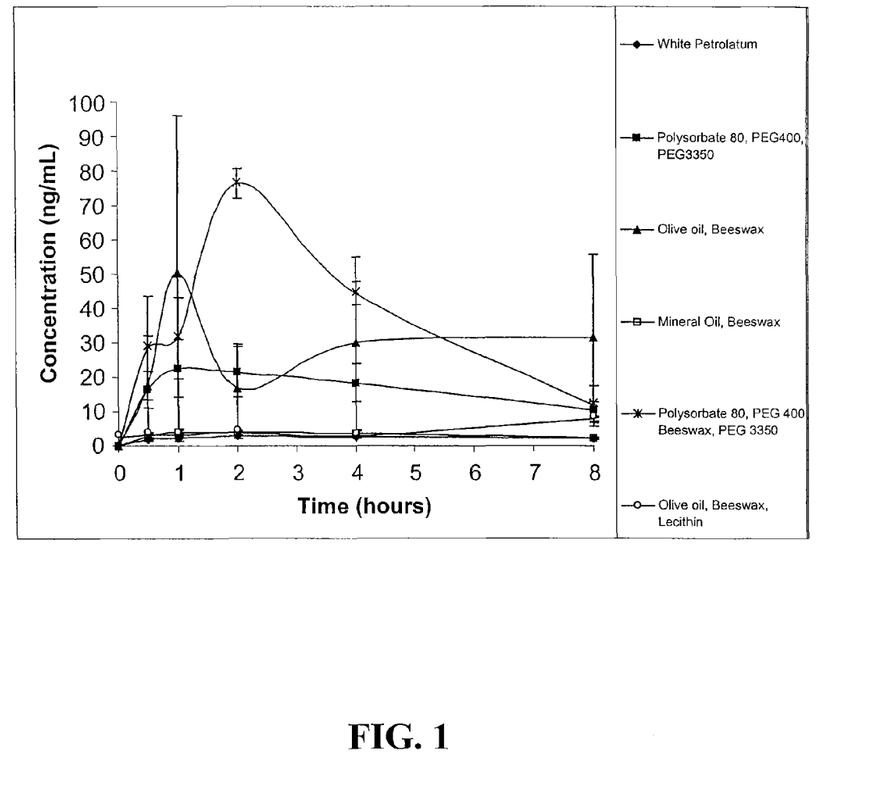
FIG. 1 shows the serum levels of M$_4$N formulations (20% M$_4$N) following intravaginal administration in Rabbits on study day 1.
Figure 2:
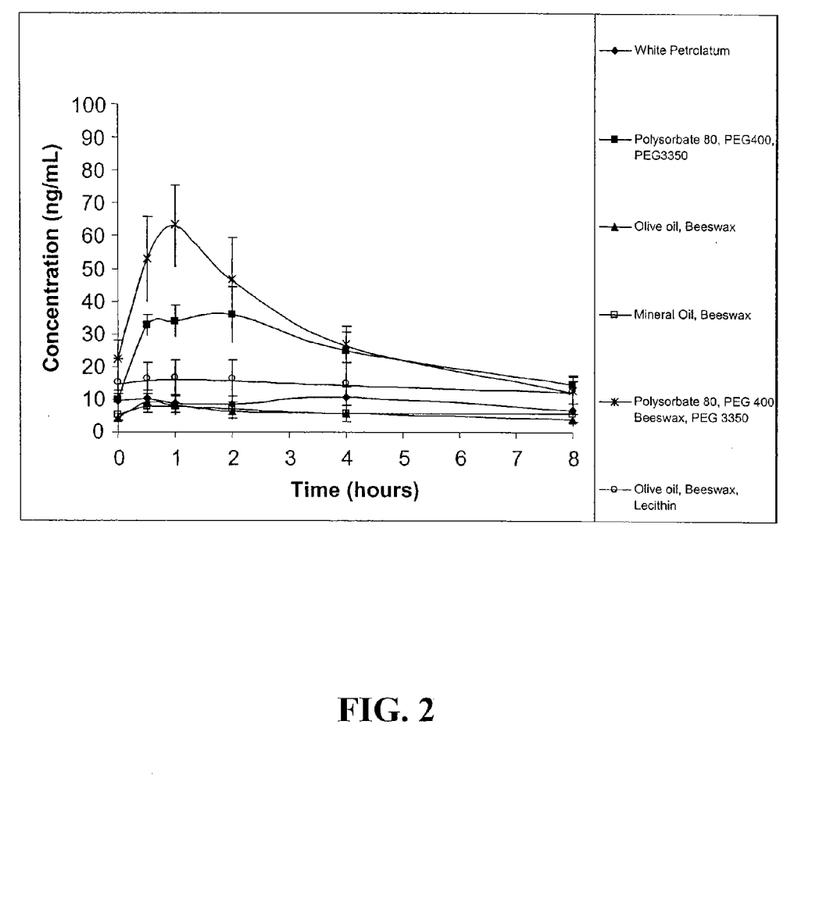
FIG. 2 shows the serum levels of M$_4$N formulations (20% M$_4$N) following intravaginal administration in Rabbits on study day 5.

Absorption of M4N occurred from all vehicles (Table 3). Blood levels after five days of dosing were typically higher then those achieved on day 1 of dosing. The highest exposure levels were generally achieved one to two hours post dosing. Serum levels of M4N varied greatly depending on excipient formulation (FIG. 1 and FIG. 2). The highest absorption occurred in the polysorbate 80, PEG 400, white beeswax and PEG 3350, and the polysorbate 80, PEG 400, and PEG 3350 groups. The mineral oil and white beeswax, and the olive oil and white beeswax groups had the lowest absorption.

Gennaro, A. R. (2003). Remington: The Science and Practice of Pharmacy, 20$^{th}$ ed., with Facts and Comparisons: DrugfactsPlus. Lippincott Williams & Williams.

Hwu, J. R. et al. (1998). Antiviral activities of methylated nordihydroguaiaretic acids. 1. Synthesis, structure identification, and inhibition of Tat-regulated HIV transactivation. *J. Med. Chem.* 41: 2994-3000.

Kloppel, G. and Luttges, J. (2004). The pathology of ductal-type pancreatic carcinomas and pancreatic intraepithelial neoplasia: insights for clinicians. *Curr. Gastroenterol. Rep.* 6(2): 111-8.

Kurman, R. J. et al. (1994). Interim guidelines for management of abnormal cervical cytology. The 1992 National Cancer Institute Workshop. *JAMA,* 271: 1866-1869.)

McDonald, R. W. et al. (2001). Synthesis and anticancer activity of nordihydroguaiaretic acid (NDGA) and analogues. *Anti-Cancer Drug Design* 16: 261-270.

O'Shaughnessy et al. (2002). Treatment and Prevention of Intraepithelial Neoplasia: An Important Target for Accelerated New Agent Development. *Clinical Cancer Res.* 8: 314-346.

TABLE 3

Serum levels of M4N in Rabbits Following Intravaginal Administration

| Group (n = 5) | Study Day | Predose | 0.5 hour | 1.0 hour | 2.0 hours | 4.0 hours | 8.0 hours |
|---|---|---|---|---|---|---|---|
| I. White petrolatum | 1 | <LLOQ | 1.63 ± 0.13$^a$ | 2.01 ± 0.45 | 2.73 ± 0.44 | 2.56 ± 0.38 | 1.97 ± 0.15 |
| I. White petrolatum | 5 | 9.51 ± 2.16 | 10.28 ± 2.58 | 8.75 ± 2.69 | 8.61 ± 2.55 | 10.79 ± 3.04 | 6.82 ± 2.21 |
| II. Polysorbate 80, PEG 400, PEG 3350 | 1 | <LLOQ | 16.41 ± 5.28 | 22.63 ± 8.51 | 21.60 ± 7.25 | 18.29 ± 5.60 | 10.51 ± 2.18 |
| II. Polysorbate 80, PEG 400, PEG 3350 | 5 | 10.07 ± 2.67 | 32.73 ± 3.12 | 33.94 ± 4.93 | 35.85 ± 8.52 | 24.90 ± 5.81 | 14.47 ± 3.08 |
| III. Olive oil, White beeswax | 1 | ND | 17.67 ± 14.62 | 50.32 ± 45.78 | 16.83 ± 12.86 | 29.86 ± 25.12 | 31.28 ± 24.26 |
| III. Olive oil, White beeswax $^b$ | 5 | 4.38 ± 1.41 | 9.11 ± 2.55 | 8.16 ± 2.88 | 6.58 ± 2.71 | 5.84 ± 2.47 | 3.84 ± 1.87 |
| IV. Mineral oil, White beeswax | 1 | ND | 3.01 ± 0.55 | 4.04 ± 1.02 | 3.80 ± 0.89 | 3.69 ± 0.71 | 2.28 ± 0.18 |
| IV. Mineral oil, White beeswax | 5 | 5.23 ± 1.55 | 7.96 ± 1.85 | 7.93 ± 1.83 | 7.21 ± 2.86 | 5.54 ± 2.22 | 5.52 ± 2.18 |
| V. Polysorbate 80, PEG 400, White beeswax, PEG 3350 | 1 | <LLOQ | 28.52 ± 14.92 | 31.48 ± 11.86 | 76.44 ± 4.18 | 44.36 ± 3.41 | 11.62 ± 5.81 |
| V. Polysorbate 80, PEG 400, White beeswax, PEG 3350 | 5 | 22.46 ± 5.76 | 52.85 ± 12.94 | 62.89 ± 12.50 | 46.26 ± 13.15 | 26.36 ± 6.17 | 12.18 ± 3.57 |
| VI. Olive oil, White beeswax, Lecithin | 1 | 2.59 ± 0.00 | 3.07 ± 0.78 | 3.25 ± 0.35 | 3.81 ± 0.49 | 2.90 ± 0.57 | 7.72 ± 0.92 |
| VI. Olive oil, White beeswax, Lecithin | 5 | 14.71 ± 7.63 | 15.51 ± 5.78 | 16.14 ± 6.04 | 15.63 ± 6.48 | 14.11 ± 7.42 | 12.18 ± 5.03 |

<LLOQ—(Low Limit of Quantitation) = 1 ng/mL
ND—Not detected
$^a$ Data are presented as mean ± standard error
$^b$ n = 4; one doe died on DS5 and was not included in analysis (death not attributed to M4N)

REFERENCES

Ansel, H. C. et al. (2004). Pharmaceutical Dosage Forms and Drug Delivery Systems eds., 8$^{th}$ ed., Lippincott Williams & Wilkins.

Aynaud, O. and Bergeron, C. (2004). Penile intraepithelial neoplasia. *Prog. Urol.* 14(1): 100-4.

Dieckmann, K. P. and Pichlmeier, U. (2004). Clinical epidemiology of testicular germ cell tumors. *World J. Urol.* 22(1): 2-14. Epub 2004 Mar. 18.

Dudney, B. W. and Malecha, M. A. (2004). Limbal stem cell deficiency following topical Mitomycin C treatment of conjunctival-corneal intraepithelial neoplasia. Am. J. Ophthalmol. 147(5): 950-1.

Garg, S. et al. (2001). Compendium of Pharmaceutical Excipients for Vaginal Formulations. Pharmaceutical Technol. Drug Delivery. Sep. 1, 2001, pp. 14-24.

Rowe, R. C. et al. eds. (2003). Handbook of Pharmaceutical Excipients. 4$^{th}$ edition. Pharmaceutical Press and American Pharmaceutical Association.

Takaori, K. et al. (2004). Pancreatic intraepithelial neoplasia. *Pancreas.* 28(3): 257-62.

The Bethesda System for reporting cervical/vaginal cytological diagnoses. (1989) National Cancer Institute Workshop. *JAMA,* 262: 931-934.

Wacker, J. and Hartschuh, W. (2004). Differential diagnosis of chronic perianal dermatitis. Premalignant and malignant disorders. *Hautarzt.* 55(3): 266-72.

Whitfield, M. L. et al. (2002). Identification of genes periodically expressed in the human cell cycle and their expression tumors. *Mol. Biol. Cell* 13(6): 1977-2000.

Zhu G. H., et al. (2002). The Sp1 transcription factor contributes to the tumor necrosis factor-induced expression of the angiogenic factor thymidine phosphorylase in human colon carcinoma cells. *Oncogene* 21(55): 8477-85.

The invention claimed is:

1. A method of treating cervical intraepithelial neoplasia or cervical intraepithelial dysplasia in a subject comprising administering to the subject having an cervical intraepithelial neoplasia or cervical intraepithelial dysplasia, a therapeutically effective amount of a pharmaceutical composition comprising a catecholic butane having the structural formula of Formula I:

wherein $R_1$ and $R_2$ are independently —H, a lower alkyl, a lower acyl, or an alkylene; $R_3$, $R_4$, $R_5$, $R_6$, $R_{10}$, $R_{11}$, $R_{12}$ and $R_{13}$ are independently —H or a lower alkyl; $R_7$, $R_8$ and $R_9$ are independently —H, —OH, a lower alkoxy, a lower acyloxy, or any two adjacent groups together may be an alkyene dioxy;

wherein the pharmaceutical composition is administered to situs of the cervical intraepithelial neoplasia or cervical intraepithelial dysplasia; and wherein the pharmaceutical composition is used to treat the cervical intraepithelial neoplasia or intraepithelial dysplasia.

2. The method of claim 1, wherein the pharmaceutical composition is administered to a genital area of the subject.

3. The method of claim 2, wherein the pharmaceutical composition is administered intravaginally to the subject.

4. The method of claim 1, wherein the catecholic butane has the structural formula of Formula II:

wherein $R_1$, $R_2$, $R_3$ and $R_4$ independently represent —OH, a lower alkoxy, a lower acyloxy, and $R_5$ and $R_6$ independently represent —H or a lower alkyl.

5. The method of claim 4, wherein the lower alkoxy is —$OCH_3$.

6. The method of claim 4, wherein the lower acyloxy is —$O(C=O)CH_3$.

7. The method of claim 4, wherein the lower alkyl is —$CH_3$.

8. The method of claim 4, wherein each of $R_5$ and $R_6$ is —$CH_3$.

9. The method of claim 4, wherein each of $R_5$ and $R_6$ is —H.

10. The method of claim 4, wherein the catecholic butane is tetra-O-methyl NDGA ($M_4N$), tri-O-methyl NDGA ($M_3N$), or di-O-methyl NDGA ($M_2N$).

11. A method of treating cervical intraepithelial neoplasia or cervical intraepithelial dysplasia in a subject comprising administering to the subject a therapeutically effective amount of a pharmaceutical composition comprising at least one of tetra-O-methyl NDGA ($M_4N$), tri-O-methyl NDGA ($M_3N$), or di-O-methyl NDGA ($M_2N$) to treat the intraepithelial neoplasia or intraepithelial dysplasia.

12. The method of claim 11, wherein the pharmaceutical composition is administered to a genital area of the subject.

13. The method of claim 12, wherein the pharmaceutical composition is administered intravaginally to the subject.

* * * * *